US010905786B2

(12) United States Patent
Shodder

(10) Patent No.: US 10,905,786 B2
(45) Date of Patent: Feb. 2, 2021

(54) STERILISATION METHOD

(71) Applicant: Regeneron Pharmaceuticals, Inc., Tarrytown, NY (US)

(72) Inventor: Philip Stephen Shodder, East Greenbush, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 16/702,909

(22) Filed: Dec. 4, 2019

(65) Prior Publication Data

US 2020/0114030 A1   Apr. 16, 2020

Related U.S. Application Data

(63) Continuation of application No. 16/498,080, filed as application No. PCT/US2018/021013 on Mar. 6, 2018.

(60) Provisional application No. 62/568,850, filed on Oct. 6, 2017, provisional application No. 62/477,030, filed on Mar. 27, 2017.

(51) Int. Cl.
*A61L 2/20* (2006.01)
*A61L 2/26* (2006.01)

(52) U.S. Cl.
CPC ............ *A61L 2/208* (2013.01); *A61L 2/26* (2013.01); *A61L 2202/122* (2013.01); *A61L 2202/15* (2013.01); *A61L 2202/24* (2013.01)

(58) Field of Classification Search
CPC .......... A61L 2202/122; A61L 2202/15; A61L 2202/24; A61L 2/0094; A61L 2/20; A61L 2/208; A61L 2/24; A61L 2/26
See application file for complete search history.

(56) References Cited

U.S. PATENT DOCUMENTS

| | | | |
|---|---|---|---|
| 5,173,258 A | * | 12/1992 | Childers ............... A61L 2/20 392/399 |
| 5,439,643 A | | 8/1995 | Liebert |
| 5,807,343 A | | 9/1998 | Tucker et al. |
| 5,807,345 A | | 9/1998 | Grabenkort |
| 5,820,603 A | | 10/1998 | Tucker et al. |
| 5,834,313 A | | 11/1998 | Lin |

(Continued)

FOREIGN PATENT DOCUMENTS

| | | |
|---|---|---|
| CN | 103083698 A | 5/2013 |
| CN | 104174058 A | 12/2014 |

(Continued)

OTHER PUBLICATIONS

Machine Translation of JP 2009 284951 (Year: 2009).*

(Continued)

*Primary Examiner* — Timothy C Cleveland
(74) *Attorney, Agent, or Firm* — Stephen J. Gaudet; Bookoff McAndrews, PLLC

(57) ABSTRACT

Embodiments of the present disclosure relate to systems and methods for the application of vaporized chemicals in the sterilization of medical products. For example, embodiments of the present disclosure may relate to systems and methods for the terminal sterilization of medical products using vaporized hydrogen peroxide (VHP). Embodiments of the present disclosure may relate to, e.g., systems and methods for the terminal sterilization of medical products, such as pre-filled syringes (PFS).

25 Claims, 7 Drawing Sheets

(56) References Cited

U.S. PATENT DOCUMENTS

| | | |
|---|---|---|
| 5,904,897 A | 5/1999 | Kendall et al. |
| 5,911,950 A | 6/1999 | Chen et al. |
| 5,919,418 A | 7/1999 | Kendall et al. |
| 5,925,316 A | 7/1999 | Kendall et al. |
| 5,961,921 A | 10/1999 | Addy et al. |
| 5,976,113 A | 11/1999 | Morigi et al. |
| 5,980,825 A | 11/1999 | Addy et al. |
| 6,030,579 A | 2/2000 | Addy et al. |
| 6,066,294 A | 5/2000 | Lin et al. |
| 6,068,817 A | 5/2000 | Addy et al. |
| 6,077,480 A | 6/2000 | Edwards et al. |
| 6,096,266 A | 8/2000 | Duroselle |
| 6,120,730 A | 9/2000 | Palaniappan et al. |
| 6,126,640 A | 10/2000 | Tucker et al. |
| 6,132,679 A | 10/2000 | Conviser |
| 6,132,680 A | 10/2000 | Addy et al. |
| 6,142,977 A | 11/2000 | Kolberg et al. |
| 6,164,044 A | 12/2000 | Porfano et al. |
| 6,174,502 B1 | 1/2001 | Addy et al. |
| 6,187,265 B1 | 2/2001 | Wu et al. |
| 6,189,195 B1 | 2/2001 | Reilly et al. |
| 6,189,292 B1 | 2/2001 | Odell et al. |
| 6,193,931 B1 | 2/2001 | Lin et al. |
| 6,203,756 B1 | 3/2001 | Lin et al. |
| 6,224,828 B1 | 5/2001 | Lin et al. |
| 6,228,324 B1 | 5/2001 | Hasegawa et al. |
| 6,250,052 B1 | 6/2001 | Porfano et al. |
| 6,263,641 B1 | 7/2001 | Odell et al. |
| 6,279,622 B1 | 8/2001 | Nguyen et al. |
| 6,319,480 B1 | 11/2001 | Addy et al. |
| 6,325,972 B1 | 12/2001 | Jacobs et al. |
| 6,390,155 B1 | 5/2002 | Nguyen |
| 6,394,111 B1 | 5/2002 | Jacobs et al. |
| 6,406,666 B1 | 6/2002 | Cicha et al. |
| 6,451,254 B1 | 9/2002 | Wang et al. |
| 6,451,255 B1 | 9/2002 | Williams et al. |
| 6,451,272 B1 | 9/2002 | Fryer et al. |
| 6,454,874 B1 | 9/2002 | Jacobs et al. |
| 6,491,881 B2 | 12/2002 | Fryer et al. |
| 6,494,964 B1 | 12/2002 | Jacobs et al. |
| 6,495,100 B1 | 12/2002 | Lin et al. |
| 6,516,817 B2 | 2/2003 | Jacobs et al. |
| 6,516,818 B2 | 2/2003 | Jacobs et al. |
| 6,528,015 B1 | 3/2003 | Lin et al. |
| 6,528,016 B1 | 3/2003 | Kohler et al. |
| 6,528,017 B2 | 3/2003 | Jacobs et al. |
| 6,530,399 B2 | 3/2003 | Nguyen et al. |
| 6,589,481 B1 | 7/2003 | Lin et al. |
| 6,627,150 B1 | 9/2003 | Wang et al. |
| 6,645,429 B1 | 11/2003 | Raniwala |
| 6,656,426 B1 | 12/2003 | Wang et al. |
| 6,656,427 B2 | 12/2003 | Lin et al. |
| 6,673,313 B2 | 1/2004 | Wang et al. |
| 6,682,696 B1 | 1/2004 | Bjerborn |
| 6,734,405 B2 | 5/2004 | Centanni et al. |
| 6,746,647 B2 | 6/2004 | Kohler et al. |
| 6,746,652 B2 | 6/2004 | Khorzad et al. |
| 6,790,410 B2 | 9/2004 | Metzner et al. |
| 6,792,743 B2 | 9/2004 | Odell et al. |
| 6,807,797 B2 | 10/2004 | Forsberg et al. |
| 6,808,681 B2 | 10/2004 | Bjerborn |
| 6,815,206 B2 | 11/2004 | Lin et al. |
| 6,852,279 B2 | 2/2005 | Williams et al. |
| 6,906,296 B2 | 6/2005 | Centanni et al. |
| 6,967,315 B2 | 11/2005 | Centanni et al. |
| 6,977,061 B2 | 12/2005 | Lin et al. |
| 6,996,952 B2 | 2/2006 | Gupta et al. |
| 7,014,813 B1 | 3/2006 | Watling et al. |
| 7,040,485 B2 | 5/2006 | Gupta et al. |
| 7,048,887 B2 | 5/2006 | Frost et al. |
| 7,108,832 B2 | 9/2006 | Christensen et al. |
| 7,179,419 B2 | 2/2007 | Lin et al. |
| 7,201,869 B2 | 4/2007 | Williams et al. |
| 7,229,590 B2 | 6/2007 | Awakowicz et al. |
| 7,229,591 B2 | 6/2007 | Wu et al. |
| 7,246,627 B2 | 7/2007 | Jacobs et al. |
| 7,252,800 B2 | 8/2007 | Jacobs et al. |
| 7,267,806 B2 | 9/2007 | Kendall et al. |
| 7,273,594 B2 | 9/2007 | Lin et al. |
| 7,285,254 B2 | 10/2007 | Lin et al. |
| 7,294,305 B2 | 11/2007 | Lin et al. |
| 7,452,504 B2 | 11/2008 | Wu et al. |
| 7,459,133 B2 | 12/2008 | Swank |
| 7,468,159 B2 | 12/2008 | Lin et al. |
| 7,481,974 B2 | 1/2009 | Sizer |
| 7,491,371 B2 | 2/2009 | Moller et al. |
| 7,550,122 B2 * | 6/2009 | Buczynski .............. A61L 2/208 422/28 |
| 7,556,767 B2 | 7/2009 | Lin et al. |
| 7,569,180 B2 | 8/2009 | Kohler et al. |
| 7,575,716 B2 | 8/2009 | Wu et al. |
| 7,582,257 B2 | 9/2009 | Bedard et al. |
| 7,604,773 B2 | 10/2009 | Ekstrom et al. |
| 7,608,218 B2 | 10/2009 | Fryer et al. |
| 7,638,090 B2 | 12/2009 | Hyde et al. |
| 7,640,782 B2 | 1/2010 | Hill |
| 7,666,369 B2 | 2/2010 | Bondar |
| 7,670,550 B2 | 3/2010 | Lin et al. |
| 7,713,473 B2 | 5/2010 | Kendall et al. |
| 7,727,464 B2 | 6/2010 | Frost |
| 7,754,156 B2 | 7/2010 | Hyde et al. |
| 7,803,316 B2 | 9/2010 | Lin et al. |
| 7,807,100 B2 | 10/2010 | Choperena et al. |
| 7,824,610 B2 | 11/2010 | Ko |
| 7,850,906 B2 | 12/2010 | Watling et al. |
| 7,880,887 B2 | 2/2011 | Olson et al. |
| 7,892,486 B2 | 2/2011 | Mizuno et al. |
| 7,910,055 B2 | 3/2011 | Bondar |
| 7,954,521 B2 | 6/2011 | Py et al. |
| 7,981,361 B2 | 7/2011 | Bacik |
| 8,017,074 B2 | 9/2011 | Arnold et al. |
| 8,029,725 B2 | 10/2011 | Olsson et al. |
| 8,034,288 B2 | 10/2011 | Burns et al. |
| 8,039,022 B2 | 10/2011 | Minamikawa et al. |
| 8,062,590 B1 | 11/2011 | Ricciardi et al. |
| 8,071,021 B2 | 12/2011 | Hill |
| 8,110,156 B2 | 2/2012 | Ricciardi et al. |
| 8,114,342 B2 | 2/2012 | Jung et al. |
| 8,118,788 B2 | 2/2012 | Frezza |
| 8,124,127 B2 | 2/2012 | Faucher et al. |
| 8,132,600 B2 | 3/2012 | Py et al. |
| 8,147,752 B2 | 4/2012 | Iwashita et al. |
| 8,147,771 B2 | 4/2012 | Yokoi et al. |
| 8,178,042 B2 | 5/2012 | Jung et al. |
| 8,196,741 B2 | 6/2012 | Finke et al. |
| 8,205,416 B2 | 6/2012 | Hansen |
| 8,221,679 B2 | 7/2012 | Golkowski |
| 8,230,616 B2 | 7/2012 | McLaren et al. |
| 8,263,016 B2 | 9/2012 | Kanner |
| 8,263,102 B2 | 9/2012 | Labrecque et al. |
| 8,268,238 B2 | 9/2012 | Bondar et al. |
| 8,268,257 B2 | 9/2012 | Frost |
| 8,277,724 B2 | 10/2012 | Jung et al. |
| 8,312,836 B2 | 11/2012 | Corbeil et al. |
| 8,323,582 B2 | 12/2012 | Ko |
| 8,329,098 B2 | 12/2012 | Kanner |
| 8,329,113 B2 | 12/2012 | Kanner |
| 8,333,931 B2 | 12/2012 | Kanner |
| 8,337,772 B2 | 12/2012 | Laumer et al. |
| 8,343,435 B2 | 1/2013 | Kanner |
| 8,349,272 B2 | 1/2013 | Hill |
| 8,357,331 B2 | 1/2013 | McVey et al. |
| 8,366,995 B2 | 2/2013 | McLaren et al. |
| 8,367,099 B2 | 2/2013 | Herweck et al. |
| 8,388,761 B2 | 3/2013 | Iwashita et al. |
| 8,425,837 B2 | 4/2013 | Carbone et al. |
| 8,428,447 B2 | 4/2013 | Von Stenglin |
| 8,431,076 B2 | 4/2013 | Fraundorfer |
| 8,431,077 B2 | 4/2013 | Goncalves |
| 8,435,459 B2 | 5/2013 | Reddy et al. |
| 8,444,919 B2 | 5/2013 | Erickson |
| 8,486,332 B1 | 7/2013 | Ricciardi et al. |
| 8,497,004 B2 | 7/2013 | Davis et al. |
| 8,506,900 B1 | 8/2013 | Ricciardi et al. |

(56) References Cited

U.S. PATENT DOCUMENTS

| | | |
|---|---|---|
| 8,529,832 B2 | 9/2013 | Lee |
| 8,574,618 B2 | 11/2013 | Herweck et al. |
| 8,574,627 B2 | 11/2013 | Martakos et al. |
| 8,591,807 B2 | 11/2013 | Berentsveig et al. |
| 8,591,808 B2 | 11/2013 | Berentsveig et al. |
| 8,621,824 B2 | 1/2014 | Mielnik et al. |
| 8,628,501 B2 | 1/2014 | Hadden |
| 8,641,982 B2 | 2/2014 | Burgmeier et al. |
| 8,652,403 B2 | 2/2014 | Reddy et al. |
| 8,658,089 B2 | 2/2014 | Berentsveig et al. |
| 8,658,092 B2 | 2/2014 | Kohler et al. |
| 8,663,555 B2 | 3/2014 | Shiosawa |
| 8,668,881 B2 * | 3/2014 | Hill .................. A61L 2/208 422/292 |
| 8,685,336 B2 | 4/2014 | Bondar |
| 8,685,337 B2 | 4/2014 | Beckmann et al. |
| 8,696,986 B2 | 4/2014 | Rovison, Jr. et al. |
| 8,703,066 B2 | 4/2014 | Vaughn et al. |
| 8,715,570 B2 | 5/2014 | Lindblad et al. |
| 8,721,983 B2 | 5/2014 | Yokoi et al. |
| 8,721,984 B2 | 5/2014 | Carbone et al. |
| 8,722,077 B2 | 5/2014 | Labrecque et al. |
| 8,722,132 B2 | 5/2014 | Labrecque et al. |
| 8,741,227 B2 | 6/2014 | Yokoi et al. |
| 8,758,679 B2 | 6/2014 | Hyde et al. |
| 8,758,681 B2 | 6/2014 | Golkowski |
| 8,765,064 B2 | 7/2014 | Yokoi et al. |
| 8,771,595 B2 | 7/2014 | Paskalov |
| 8,790,576 B2 | 7/2014 | Bauer et al. |
| 8,808,622 B2 | 8/2014 | Arnold et al. |
| 8,808,631 B2 | 8/2014 | Hill et al. |
| 8,821,807 B2 | 9/2014 | Schwartz et al. |
| 8,834,790 B2 | 9/2014 | Boschi et al. |
| 8,834,808 B2 | 9/2014 | Drenguis |
| 8,840,836 B2 | 9/2014 | Olson |
| 8,858,978 B2 | 10/2014 | Labrecque et al. |
| 8,865,066 B2 | 10/2014 | Rovison et al. |
| 8,871,145 B2 | 10/2014 | Paskalov |
| 8,894,926 B2 | 11/2014 | Hanada et al. |
| 8,919,359 B2 | 12/2014 | Iwashita et al. |
| 8,932,535 B2 | 1/2015 | Hyde et al. |
| 8,940,245 B2 | 1/2015 | Reddy et al. |
| 8,945,468 B2 | 2/2015 | Reddy et al. |
| 8,961,872 B2 | 2/2015 | Fehr et al. |
| 8,962,023 B2 | 2/2015 | Labrecque et al. |
| 8,974,730 B2 | 3/2015 | Burns et al. |
| 8,974,737 B2 | 3/2015 | Erickson |
| 8,992,837 B2 | 3/2015 | Jung et al. |
| 8,992,853 B2 | 3/2015 | Stratman et al. |
| 9,022,079 B2 | 5/2015 | Py et al. |
| 9,028,749 B2 | 5/2015 | Ryu et al. |
| 9,034,249 B2 | 5/2015 | Foreman et al. |
| 9,050,385 B2 | 6/2015 | Weinberger et al. |
| 9,078,435 B2 | 7/2015 | Dunn |
| 9,078,943 B2 | 7/2015 | Herold et al. |
| 9,101,679 B2 | 8/2015 | Robitaille et al. |
| 9,108,835 B2 | 8/2015 | Hayakawa et al. |
| 9,120,660 B2 | 9/2015 | Sangi et al. |
| 9,120,661 B2 | 9/2015 | Sangi et al. |
| 9,125,960 B2 | 9/2015 | Stratman et al. |
| 9,138,005 B2 | 9/2015 | Berentsveig et al. |
| 9,156,576 B2 | 10/2015 | Pjanic et al. |
| 9,173,968 B2 | 11/2015 | Hanada |
| 9,180,217 B2 | 11/2015 | Arnold et al. |
| 9,192,164 B2 | 11/2015 | Berentsveig et al. |
| 9,213,341 B2 | 12/2015 | Hill |
| 9,220,631 B2 | 12/2015 | Sigg et al. |
| 9,220,820 B2 | 12/2015 | Faucher et al. |
| 9,241,491 B2 | 1/2016 | Berentsveig et al. |
| 9,242,753 B2 | 1/2016 | Gay et al. |
| 9,254,343 B2 | 2/2016 | Herold et al. |
| 9,295,744 B2 | 3/2016 | Rovison et al. |
| 9,302,021 B2 | 4/2016 | Klobusnik |
| 9,320,819 B2 | 4/2016 | Koyama |
| 9,320,820 B2 | 4/2016 | Rovison, Jr. et al. |
| 9,339,573 B2 | 5/2016 | Seidenberg et al. |
| 9,364,571 B2 | 6/2016 | Ahiska |
| 9,402,928 B2 | 8/2016 | Tremblay et al. |
| 9,403,330 B2 | 8/2016 | Laumer et al. |
| 9,408,931 B1 | 8/2016 | Ricciardi et al. |
| 9,408,965 B2 | 8/2016 | Christensen |
| 9,410,191 B2 | 8/2016 | Alvarez, Jr. et al. |
| 9,427,485 B2 | 8/2016 | Tremblay et al. |
| 9,439,991 B2 | 9/2016 | Schwartz et al. |
| 9,452,231 B2 | 9/2016 | Nonnenmacher |
| 9,457,114 B2 | 10/2016 | Loy |
| 9,463,259 B2 | 10/2016 | Hanada |
| 9,474,815 B2 | 10/2016 | Dufresne et al. |
| 9,480,763 B2 | 11/2016 | Dufresne et al. |
| 9,480,764 B2 | 11/2016 | Tremblay et al. |
| 9,480,765 B2 | 11/2016 | Tremblay et al. |
| 9,498,549 B2 | 11/2016 | Kanno et al. |
| 9,505,598 B2 | 11/2016 | Niehr et al. |
| 9,522,202 B1 | 12/2016 | Ahiska et al. |
| 9,522,205 B2 | 12/2016 | Ahiska |
| 9,533,065 B2 | 1/2017 | Foreman et al. |
| 9,539,352 B2 | 1/2017 | Keener et al. |
| 9,541,487 B2 | 1/2017 | Saito et al. |
| 9,555,146 B2 | 1/2017 | Fehr et al. |
| 9,561,297 B2 | 2/2017 | Kreber |
| 9,566,360 B2 | 2/2017 | Morikawa et al. |
| 9,566,361 B2 | 2/2017 | Morikawa et al. |
| 9,592,324 B2 | 3/2017 | Herweck et al. |
| 9,593,004 B2 | 3/2017 | Hayakawa et al. |
| 9,597,377 B2 | 3/2017 | Fan |
| 9,603,739 B2 | 3/2017 | Lerner |
| 9,604,740 B2 | 3/2017 | Py |
| 9,610,559 B2 | 4/2017 | Riskin et al. |
| 9,616,368 B2 | 4/2017 | Turbett et al. |
| 9,617,135 B2 | 4/2017 | Hayakawa et al. |
| 9,617,136 B2 | 4/2017 | Hayakawa et al. |
| 9,629,936 B2 | 4/2017 | Salmisuo |
| 9,637,604 B2 | 5/2017 | Ito et al. |
| 9,662,412 B2 | 5/2017 | Ferrell et al. |
| 9,662,450 B2 | 5/2017 | Jones et al. |
| 9,675,763 B2 | 6/2017 | Huet |
| 9,682,163 B2 | 6/2017 | Loy et al. |
| 9,682,175 B2 | 6/2017 | Labrecque et al. |
| 9,694,095 B2 | 7/2017 | Paskalov |
| RE46,510 E | 8/2017 | Odell et al. |
| 9,724,438 B2 | 8/2017 | Turbett |
| 9,750,832 B2 | 9/2017 | Paver, Jr. |
| 9,766,012 B2 | 9/2017 | McLaren et al. |
| 9,775,924 B2 | 10/2017 | Tanimoto et al. |
| 9,802,726 B2 | 10/2017 | Mielnik et al. |
| 9,814,795 B2 | 11/2017 | Dufresne et al. |
| 9,814,796 B2 | 11/2017 | Dunn |
| 2001/0031221 A1 | 10/2001 | Wu et al. |
| 2002/0081228 A1 | 6/2002 | Hui et al. |
| 2002/0098111 A1 | 7/2002 | Nguyen et al. |
| 2002/0119075 A1 | 8/2002 | Jacobs et al. |
| 2002/0122744 A1 | 9/2002 | Hui et al. |
| 2003/0049165 A1 | 3/2003 | Yamamoto et al. |
| 2003/0063997 A1 | 4/2003 | Fryer et al. |
| 2003/0138347 A1 | 7/2003 | Lin |
| 2004/0028556 A1 | 2/2004 | Frost et al. |
| 2004/0170527 A1 | 9/2004 | Jacobs et al. |
| 2004/0191114 A1 | 9/2004 | Frost et al. |
| 2005/0042130 A1 | 2/2005 | Lin et al. |
| 2005/0163655 A1 | 7/2005 | Lin et al. |
| 2006/0008378 A1 | 1/2006 | Imai et al. |
| 2006/0067856 A1 | 3/2006 | Martensson et al. |
| 2006/0067976 A1 | 3/2006 | Ferraro et al. |
| 2006/0088596 A1 | 4/2006 | Labrecque et al. |
| 2006/0280646 A1 | 12/2006 | Shiosawa |
| 2007/0003432 A1 | 1/2007 | Christensen et al. |
| 2007/0006551 A1 | 1/2007 | Sizer |
| 2007/0014691 A1 | 1/2007 | Lin et al. |
| 2007/0048177 A1 | 3/2007 | Lin et al. |
| 2007/0084144 A1 | 4/2007 | Labrecque et al. |
| 2007/0098591 A1 | 5/2007 | Frinke et al. |
| 2007/0172383 A1 | 7/2007 | Williams et al. |
| 2007/0231188 A1 | 10/2007 | Jung et al. |
| 2007/0231192 A1 | 10/2007 | Jung et al. |

(56) References Cited

U.S. PATENT DOCUMENTS

| | | |
|---|---|---|
| 2007/0231193 A1 | 10/2007 | Jung et al. |
| 2007/0231194 A1 | 10/2007 | Jung et al. |
| 2007/0231201 A1 | 10/2007 | Roberts et al. |
| 2007/0231202 A1 | 10/2007 | Roberts et al. |
| 2007/0258873 A1 | 11/2007 | Wu et al. |
| 2007/0292305 A1 | 12/2007 | Dempsey et al. |
| 2008/0025869 A1 | 1/2008 | Kendall et al. |
| 2008/0085223 A1 | 4/2008 | Jung et al. |
| 2008/0131342 A1 | 6/2008 | Wu et al. |
| 2008/0202961 A1 | 8/2008 | Sharp |
| 2008/0226496 A1 | 9/2008 | Rivkine et al. |
| 2008/0233251 A1 | 9/2008 | Sizer |
| 2008/0279736 A1 | 11/2008 | Frinke et al. |
| 2009/0071104 A1 | 3/2009 | Fischer |
| 2009/0110596 A1 | 4/2009 | Christensen et al. |
| 2009/0123330 A1 | 5/2009 | Moller et al. |
| 2009/0208378 A1 | 8/2009 | Jung et al. |
| 2009/0232697 A1 | 9/2009 | Martensson et al. |
| 2009/0232703 A1 | 9/2009 | Jung et al. |
| 2009/0324445 A1 | 12/2009 | Kohler et al. |
| 2010/0034697 A1 | 2/2010 | Weinberger et al. |
| 2010/0086447 A1 | 4/2010 | Jung et al. |
| 2010/0090837 A1 | 4/2010 | Jung et al. |
| 2010/0172795 A1 | 7/2010 | Lothar |
| 2011/0176959 A1 | 7/2011 | Ko |
| 2011/0217204 A1 | 9/2011 | Franciskovich et al. |
| 2011/0280765 A1 | 11/2011 | Hirose et al. |
| 2012/0009085 A1 | 1/2012 | Burger |
| 2012/0114524 A1 | 5/2012 | Sigg |
| 2012/0189495 A1 | 7/2012 | Franciskovich et al. |
| 2012/0213672 A1 | 8/2012 | Adams et al. |
| 2012/0230870 A1 | 9/2012 | Franciskovich et al. |
| 2013/0004380 A1 | 1/2013 | Yoo |
| 2013/0004384 A1 | 1/2013 | Yoo |
| 2013/0028794 A1 | 1/2013 | Silvestri et al. |
| 2013/0084215 A1 | 4/2013 | Fukui et al. |
| 2013/0105025 A1 | 5/2013 | Fehr et al. |
| 2013/0156641 A1 | 6/2013 | Paskalov |
| 2013/0236359 A1 | 9/2013 | Burger |
| 2013/0296779 A1 | 11/2013 | Kuehne et al. |
| 2014/0020331 A1 | 1/2014 | Chin et al. |
| 2014/0109519 A1 | 4/2014 | Hayakawa et al. |
| 2014/0109529 A1 | 4/2014 | Hayakawa et al. |
| 2014/0154132 A1 | 6/2014 | Frieze et al. |
| 2014/0170020 A1 | 6/2014 | Hiruta |
| 2014/0193299 A1 | 7/2014 | Leamy et al. |
| 2014/0205507 A1 | 7/2014 | Yokoi et al. |
| 2014/0223862 A1 | 8/2014 | Nicoletti et al. |
| 2014/0241953 A1 | 8/2014 | Lho et al. |
| 2014/0288511 A1 | 9/2014 | Tan-Malecki et al. |
| 2014/0301895 A1 | 10/2014 | Opie et al. |
| 2015/0010432 A1 | 1/2015 | Olson |
| 2015/0037204 A1 | 2/2015 | Geiger et al. |
| 2015/0037205 A1 | 2/2015 | Miyahara et al. |
| 2015/0044094 A1 | 2/2015 | Cadieux et al. |
| 2015/0078961 A1 | 3/2015 | Opie |
| 2015/0105734 A1 | 4/2015 | Bryant et al. |
| 2015/0182651 A1 | 7/2015 | Tanimoto et al. |
| 2015/0183540 A1 | 7/2015 | Lothar |
| 2015/0190566 A1 | 7/2015 | Okihara |
| 2015/0197359 A1 | 7/2015 | Nohara et al. |
| 2015/0205985 A1 | 7/2015 | Jinadatha |
| 2015/0208648 A1 | 7/2015 | Iwashita et al. |
| 2015/0209455 A1 | 7/2015 | Turbett et al. |
| 2015/0239594 A1 | 8/2015 | Batema |
| 2015/0273097 A1 | 10/2015 | Murayama et al. |
| 2015/0274397 A1 | 10/2015 | Dunn |
| 2015/0305342 A1 | 10/2015 | Burke et al. |
| 2015/0305343 A1 | 10/2015 | Burke et al. |
| 2015/0305344 A1 | 10/2015 | Burke et al. |
| 2015/0306259 A1 | 10/2015 | Deutschle et al. |
| 2015/0306266 A1 | 10/2015 | Burke et al. |
| 2015/0313250 A1 | 11/2015 | Itarashiki et al. |
| 2015/0320503 A1 | 11/2015 | Bezdikian |
| 2015/0335826 A1 | 11/2015 | Huet |
| 2015/0352238 A1 | 12/2015 | Dufresne et al. |
| 2015/0373986 A1 | 12/2015 | Burke et al. |
| 2016/0009433 A1 | 1/2016 | Tanaka et al. |
| 2016/0090205 A1 | 3/2016 | Py et al. |
| 2016/0121010 A1 | 5/2016 | Harada et al. |
| 2016/0166765 A1 | 6/2016 | Tan-Malecki et al. |
| 2016/0183522 A1 | 6/2016 | Rovison et al. |
| 2016/0185474 A1 | 6/2016 | Bronner et al. |
| 2016/0193375 A1 | 7/2016 | Laflamme et al. |
| 2016/0199578 A1 | 7/2016 | Tan-Malecki et al. |
| 2016/0199582 A1 | 7/2016 | Tan-Malecki et al. |
| 2016/0199583 A1 | 7/2016 | Tan-Malecki et al. |
| 2016/0200461 A1 | 7/2016 | Broadbent et al. |
| 2016/0206767 A1 | 7/2016 | Park et al. |
| 2016/0235873 A1 | 8/2016 | Rovison, Jr. et al. |
| 2016/0235877 A1 | 8/2016 | Ruley et al. |
| 2016/0250367 A1 | 9/2016 | Hijikata et al. |
| 2016/0257054 A1 | 9/2016 | Hayakawa et al. |
| 2016/0257055 A1 | 9/2016 | Hayakawa et al. |
| 2016/0263269 A1 | 9/2016 | Hayakawa et al. |
| 2016/0272347 A1 | 9/2016 | Procyshyn et al. |
| 2016/0296652 A1 | 10/2016 | Leamy et al. |
| 2016/0303791 A1 | 10/2016 | Hannafin et al. |
| 2016/0317688 A1 | 11/2016 | Deprey et al. |
| 2016/0324998 A1 | 11/2016 | Reed et al. |
| 2016/0325482 A1 | 11/2016 | Hayakawa et al. |
| 2016/0347492 A1 | 12/2016 | Lu et al. |
| 2016/0348160 A1 | 12/2016 | Alvarez, Jr. et al. |
| 2016/0361450 A1 | 12/2016 | Dufresne et al. |
| 2016/0375160 A1 | 12/2016 | Hayakawa |
| 2016/0375167 A1 | 12/2016 | Min et al. |
| 2017/0001744 A1 | 1/2017 | Konze et al. |
| 2017/0007729 A1 | 1/2017 | Bertomeu Asategui |
| 2017/0014539 A1 | 1/2017 | Min et al. |
| 2017/0027175 A1 | 2/2017 | Dunn |
| 2017/0035922 A1 | 2/2017 | Stratman et al. |
| 2017/0056541 A1 | 3/2017 | Sveningsson |
| 2017/0056923 A1 | 3/2017 | Hioki et al. |
| 2017/0072081 A1 | 3/2017 | Alvarez, Jr. et al. |
| 2017/0100284 A1 | 4/2017 | Lerner |
| 2017/0100306 A1 | 4/2017 | Weikart et al. |
| 2017/0100542 A1 | 4/2017 | Norton et al. |
| 2017/0100543 A1 | 4/2017 | Cabiri et al. |
| 2017/0106109 A1 | 4/2017 | Morikawa et al. |
| 2017/0107008 A1 | 4/2017 | Ichikawa |
| 2017/0129635 A1 | 5/2017 | Hijikata et al. |
| 2017/0157316 A1 | 6/2017 | Browne |
| 2017/0158365 A1 | 6/2017 | Py |
| 2017/0166341 A1 | 6/2017 | Hayakawa et al. |
| 2017/0166342 A1 | 6/2017 | Hayakawa et al. |
| 2017/0173267 A1 | 6/2017 | Ashmead et al. |
| 2017/0175069 A1 | 6/2017 | Baker, Jr. et al. |
| 2017/0182259 A1 | 6/2017 | Fukushi et al. |
| 2017/0189619 A1 | 7/2017 | Constantineau et al. |
| 2017/0189843 A1 | 7/2017 | Turbett et al. |
| 2017/0197003 A1 | 7/2017 | Taggart |
| 2017/0197024 A1 | 7/2017 | Kiminami et al. |
| 2017/0203043 A1 | 7/2017 | Rusch et al. |
| 2017/0203052 A1 | 7/2017 | Abe et al. |
| 2017/0203869 A1 | 7/2017 | Lucani et al. |
| 2017/0208802 A1 | 7/2017 | Franciskovich et al. |
| 2017/0217617 A1 | 8/2017 | Sato et al. |
| 2017/0217661 A1 | 8/2017 | Erickson |
| 2017/0224435 A1 | 8/2017 | Godfrey et al. |
| 2017/0224858 A1 | 8/2017 | Stibich |
| 2017/0258633 A1 | 9/2017 | Vure et al. |
| 2017/0275581 A1 | 9/2017 | Nishimura et al. |
| 2017/0281876 A1 | 10/2017 | Odell et al. |
| 2017/0304476 A1 | 10/2017 | Taggart et al. |
| 2017/0312378 A1 | 11/2017 | Goncalves |
| 2017/0326262 A1 | 11/2017 | Paver, Jr. |

FOREIGN PATENT DOCUMENTS

| | | |
|---|---|---|
| CN | 205515660 U | 8/2016 |
| EP | 0901380 A1 | 3/1999 |
| EP | 1019120 A1 | 7/2000 |
| EP | 1061974 A1 | 12/2000 |
| EP | 0846072 B1 | 5/2001 |

(56) References Cited

FOREIGN PATENT DOCUMENTS

| | | |
|---|---|---|
| EP | 0774263 B1 | 3/2003 |
| EP | 1368066 A1 | 12/2003 |
| EP | 0880972 B1 | 2/2004 |
| EP | 1061975 B1 | 2/2004 |
| EP | 0971749 B1 | 7/2004 |
| EP | 0976415 B1 | 5/2005 |
| EP | 1759715 A1 | 3/2007 |
| EP | 1764115 A1 | 3/2007 |
| EP | 1675632 B1 | 9/2007 |
| EP | 1829577 A2 | 9/2007 |
| EP | 1884250 A1 | 2/2008 |
| EP | 1071487 B1 | 3/2008 |
| EP | 1924309 A1 | 5/2008 |
| EP | 1818069 B1 | 9/2008 |
| EP | 1973592 A2 | 10/2008 |
| EP | 2121085 A1 | 11/2009 |
| EP | 1735014 B1 | 8/2010 |
| EP | 2253548 A1 | 11/2010 |
| EP | 2253549 A1 | 11/2010 |
| EP | 2453928 A1 | 5/2012 |
| EP | 2593369 A1 | 5/2013 |
| EP | 2162652 B1 | 9/2013 |
| EP | 2125530 B1 | 12/2013 |
| EP | 2730512 A1 | 5/2014 |
| EP | 2744523 A2 | 6/2014 |
| EP | 2846754 A1 | 3/2015 |
| EP | 2854762 A1 | 4/2015 |
| EP | 2862587 A1 | 4/2015 |
| EP | 1940476 B1 | 5/2015 |
| EP | 2869813 A1 | 5/2015 |
| EP | 2436407 B1 | 6/2015 |
| EP | 2436408 B1 | 6/2015 |
| EP | 1433705 B1 | 7/2015 |
| EP | 2687478 B1 | 8/2015 |
| EP | 2939649 A1 | 11/2015 |
| EP | 2604294 B1 | 12/2015 |
| EP | 3009152 A1 | 4/2016 |
| EP | 3037379 A1 | 6/2016 |
| EP | 3 056 223 A1 | 8/2016 |
| EP | 1019120 B1 | 8/2016 |
| EP | 3056223 A1 | 8/2016 |
| EP | 3057633 A1 | 8/2016 |
| EP | 3070011 A1 | 9/2016 |
| EP | 2387422 B1 | 10/2016 |
| EP | 2949585 B1 | 12/2016 |
| EP | 3108902 A1 | 12/2016 |
| EP | 3130359 A1 | 2/2017 |
| EP | 2394950 B1 | 4/2017 |
| EP | 2925392 B1 | 4/2017 |
| EP | 2407181 B1 | 5/2017 |
| EP | 3160471 A1 | 5/2017 |
| EP | 3162401 A2 | 5/2017 |
| EP | 3170756 A1 | 5/2017 |
| EP | 3192549 A1 | 7/2017 |
| EP | 2944583 B1 | 8/2017 |
| EP | 3017830 B1 | 8/2017 |
| EP | 3199189 A1 | 8/2017 |
| EP | 3202389 A1 | 8/2017 |
| EP | 3202447 A1 | 8/2017 |
| EP | 3202705 A1 | 8/2017 |
| EP | 3213786 A1 | 9/2017 |
| JP | 2009 284951 A | 12/2009 |
| WO | WO 1995/012418 A1 | 5/1995 |
| WO | WO-9708054 A1 | 3/1997 |
| WO | WO-9744068 A1 | 11/1997 |
| WO | WO-9807453 A1 | 2/1998 |
| WO | WO-9819715 A1 | 5/1998 |
| WO | WO-9848856 A1 | 11/1998 |
| WO | WO-9856438 A1 | 12/1998 |
| WO | WO-9915215 A1 | 4/1999 |
| WO | WO-9927971 A2 | 6/1999 |
| WO | WO-9945984 A1 | 9/1999 |
| WO | WO-9945985 A1 | 9/1999 |
| WO | WO-02072157 A1 | 9/2002 |
| WO | WO-2005032627 A1 | 4/2005 |
| WO | WO-2005067984 A1 | 7/2005 |
| WO | WO-2006047325 A1 | 5/2006 |
| WO | WO-2007024957 A1 | 3/2007 |
| WO | WO-2007035621 A1 | 3/2007 |
| WO | WO-2007083034 A2 | 7/2007 |
| WO | WO-2008110890 A1 | 9/2008 |
| WO | WO-2008111893 A1 | 9/2008 |
| WO | WO-2009092430 A1 | 7/2009 |
| WO | WO-2011006877 A1 | 1/2011 |
| WO | WO-2011038487 A1 | 4/2011 |
| WO | WO-2011115428 A2 | 9/2011 |
| WO | WO-2011117878 A1 | 9/2011 |
| WO | WO-2011125133 A1 | 10/2011 |
| WO | WO-2012007056 A1 | 1/2012 |
| WO | WO-2012075547 A1 | 6/2012 |
| WO | WO-2012173562 A1 | 12/2012 |
| WO | WO-2013028537 A2 | 2/2013 |
| WO | WO-2013178771 A1 | 12/2013 |
| WO | WO-2013184270 A1 | 12/2013 |
| WO | WO-2014005728 A1 | 1/2014 |
| WO | WO-2014049712 A1 | 4/2014 |
| WO | WO-2014049714 A1 | 4/2014 |
| WO | WO-2014102987 A1 | 7/2014 |
| WO | WO-2014187779 A1 | 11/2014 |
| WO | WO-2015055608 A1 | 4/2015 |
| WO | WO-2015135887 A1 | 9/2015 |
| WO | WO-2016052037 A1 | 4/2016 |
| WO | WO-2016064288 A1 | 4/2016 |
| WO | WO-2016068333 A1 | 5/2016 |
| WO | WO-2016094658 A1 | 6/2016 |
| WO | WO-2016140449 A1 | 9/2016 |
| WO | WO-2016165976 A1 | 10/2016 |
| WO | WO-2016180855 A1 | 11/2016 |
| WO | WO-2016186502 A2 | 11/2016 |
| WO | WO-2016191535 A2 | 12/2016 |
| WO | WO-2017027876 A1 | 2/2017 |
| WO | WO-2017030195 A1 | 2/2017 |
| WO | WO-2017055462 A1 | 4/2017 |
| WO | WO-2017057477 A1 | 4/2017 |
| WO | WO-2017062407 A1 | 4/2017 |
| WO | WO-2017062930 A1 | 4/2017 |
| WO | WO-2017062931 A1 | 4/2017 |
| WO | WO-2017062933 A1 | 4/2017 |
| WO | WO-2017087798 A1 | 5/2017 |
| WO | WO-2017087871 A1 | 5/2017 |
| WO | WO-2017089197 A1 | 6/2017 |
| WO | WO-2017103954 A1 | 6/2017 |
| WO | WO-2017119582 A1 | 7/2017 |
| WO | WO-2017126550 A1 | 7/2017 |
| WO | WO-2017129232 A1 | 8/2017 |
| WO | WO-2017129685 A1 | 8/2017 |
| WO | WO-2017137665 A1 | 8/2017 |
| WO | WO-2017139375 A1 | 8/2017 |
| WO | WO-2017139573 A1 | 8/2017 |
| WO | WO-2017158805 A1 | 9/2017 |

OTHER PUBLICATIONS

International Search Report and Written Opinion for PCT/US2018/021013, dated May 11, 2018 (13 pages).

Fischer et al., "Specific Immune Response to Phospholipase B-Like 2 Protein, a Host Cell Impurity in Lebrikizumab Clinical Material," The AAPS Journal, vol. 19, No. 1, pp. 254-263, Oct. 13, 2016 (10 pages).

* cited by examiner

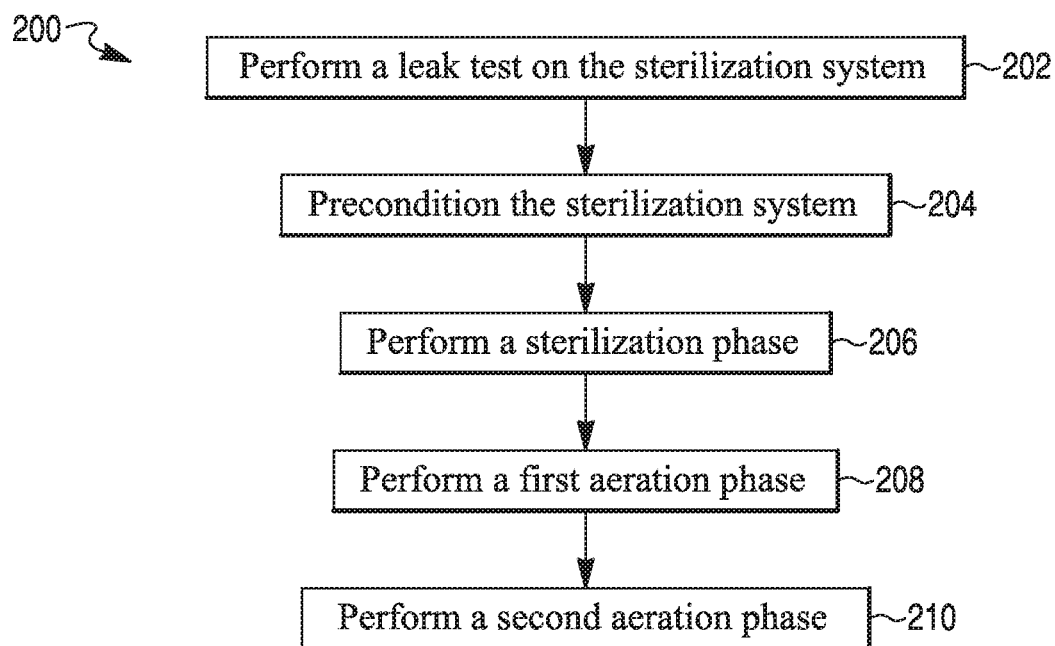

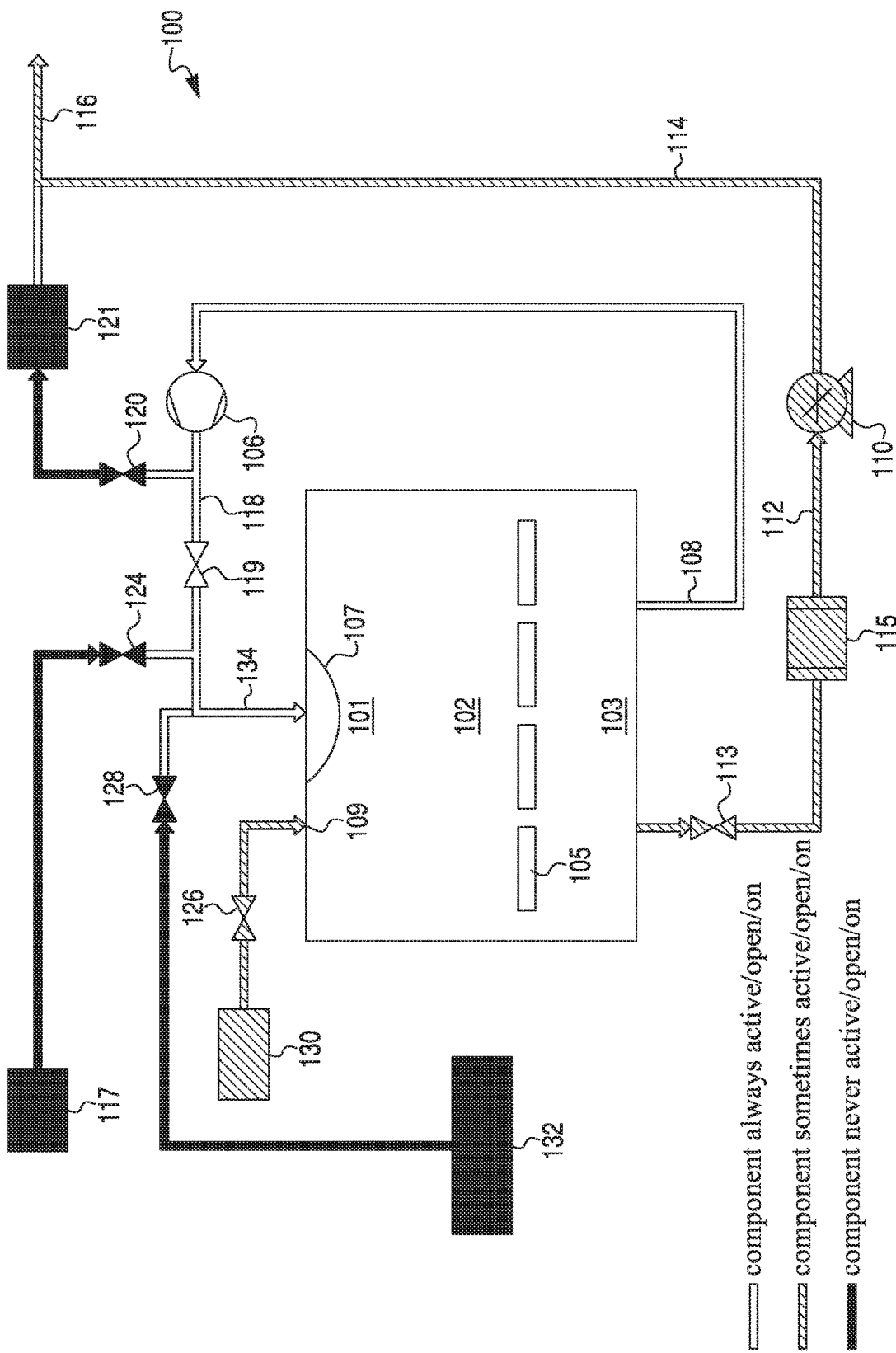

STERILISATION METHOD

CROSS-REFERENCE TO RELATED APPLICATIONS

This application is a continuation of U.S. application Ser. No. 16/498,080, filed Sep. 26, 2019, which is a U.S. national stage filing under 35 U.S.C. § 371 of International Application No. PCT/US2018/021013, filed Mar. 6, 2018, which claims priority to U.S. Application No. 62/477,030, filed Mar. 27, 2017, and U.S. Application No. 62/568,850, filed Oct. 6, 2017. All of which are incorporated by reference herein in their entireties.

FIELD OF THE DISCLOSURE

Various embodiments of the present disclosure relate to systems and methods for sterilization of medical products. More specifically, particular embodiments of the present disclosure relate to systems and methods for moist chemical sterilization of medical products, including terminal sterilization of pre-filled syringes (or other pre-filled drug delivery devices) using vaporized chemicals, such as vaporized hydrogen peroxide.

BRIEF DESCRIPTION OF THE DRAWINGS

The accompanying drawings, which are incorporated into and constitute a part of this specification, illustrate various exemplary embodiments and, together with the description, serve to explain the principles of the disclosed embodiments. The drawings show different aspects of the present disclosure and, where appropriate, reference numerals illustrating like structures, components, materials and/or elements in different figures are labeled similarly. It is understood that various combinations of the structures, components, and/or elements, other than those specifically shown, are contemplated and are within the scope of the present disclosure.

There are many inventions described and illustrated herein. The described inventions are neither limited to any single aspect nor embodiment thereof, nor to any combinations and/or permutations of such aspects and/or embodiments. Moreover, each of the aspects of the described inventions, and/or embodiments thereof, may be employed alone or in combination with one or more of the other aspects of the described inventions and/or embodiments thereof. For the sake of brevity, certain permutations and combinations are not discussed and/or illustrated separately herein. Notably, an embodiment or implementation described herein as "exemplary" is not to be construed as preferred or advantageous, for example, over other embodiments or implementations; rather, it is intended reflect or indicate the embodiment(s) is/are "example" embodiment(s).

FIG. 2 is a flow diagram of steps in an exemplary method of sterilizing medical products using vaporized chemicals.

FIGS. 4A-4C are schematic drawings of an exemplary sterilization system at various stages in an exemplary method of sterilizing medical products using vaporized chemicals.

DETAILED DESCRIPTION

Figure 1:
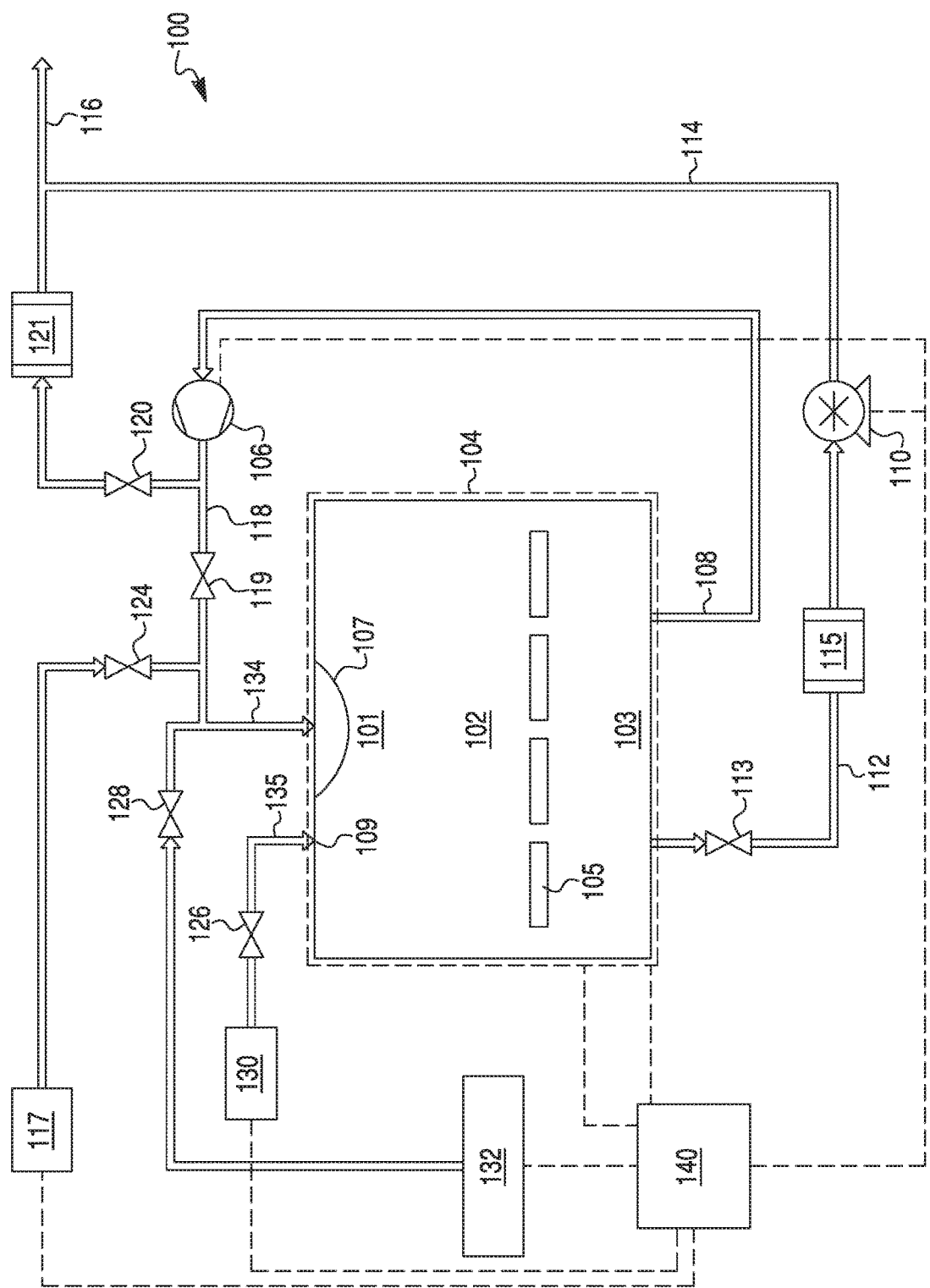
FIG. 1 is a schematic drawing of an exemplary sterilization system that may be used for sterilization of medical products.

As used herein, the terms "comprises," "comprising," "include," "have," "with," or any other variation thereof, are intended to cover a non-exclusive inclusion, such that a process, method, article, or apparatus that comprises a list of elements need not include only those elements, but may include other elements not expressly listed or inherent to such process, method, article, or apparatus. The term "exemplary" is used in the sense of "example," rather than "ideal." Any implementation described herein as exemplary is not to be construed as preferred or advantageous over other implementations. Further, the terms "first," "second," and the like, herein do not denote any order, quantity, or importance, but rather are used to distinguish one element from another. Similarly, terms of relative orientation, such as "front side," "top side," "back side," "bottom side," "upper," "lower," etc. are referenced relative to the described figures.

As used herein, the terms "about" and "approximately" are meant to account for possible variation of ±10% in a stated numeric value. All measurements reported herein are understood to be modified by the term "about," or the term "approximately," whether or not those terms are explicitly used, unless explicitly stated otherwise. As used herein, the singular forms "a," "an," and "the" include plural referents unless the context clearly dictates otherwise. Moreover, in the claims, values, limits, and/or ranges means the value, limit, and/or range+/−10%.

As used in the present disclosure, the term "sterilization" refers to achieving a level of sterility appropriate for a formulated drug substance or drug product for commercial distribution and use. Such a level of sterility may be defined in, for example, regulatory guidelines or regulations, such as guidelines released by the U.S. Food and Drug Administration. In some embodiments, such a level of sterility may include, for example, a 6-log reduction in microbial populations of biological indicators placed on an outside or inside surface of a drug product (e.g., an outside surface of a syringe or an inside surface of a blister pack). In other embodiments, such a level of sterility may include, for example, a 9-log or 12-log reduction in microbial populations of biological indicators. Sterilization refers to achieving such an appropriate level of sterility while also achieving a sufficiently low level of residual sterilizing chemicals (e.g., vaporized hydrogen peroxide, ethylene oxide, etc.) for commercial distribution and use. Such a low level of residual sterilizing chemical may also be defined in regulatory guidelines or regulations.

As used in the present disclosure, the term "terminal sterilization" refers to the sterilization of a drug product in a container or packaging, such as in a primary packaging component, or in both primary and secondary packaging components, suitable for commercial distribution and use.

As used in the present disclosure, the term "medical product" refers to a product for medical use on a living animal. The term "medical product" includes, for example, drug products, formulated drug substances, medical implants, medical instruments, or combinations thereof. For example, the term "medical product" may refer to a syringe containing a formulated drug substance, such as a parenteral or an ophthalmic syringe. Other exemplary medical products include, e.g., suppository applicators and medication, transdermal drug delivery devices, medical implants, needles, cannulas, medical instruments, and any other product requiring sterilization prior to an intended medical use.

As used in the present disclosure, the term "formulated drug substance" refers to a composition containing at least one active ingredient (e.g., a small molecule, a protein, a nucleic acid, or a gene therapy medicament) and an excipient, prepared for medical distribution and use. A formulated drug substance may include fillers, coloring agents, and other active or inactive ingredients.

As used in the present disclosure, the term "drug product" refers to a dosage form that contains a formulated drug substance, such as a finished dosage form for an active ingredient. A drug product may include packaging for commercial distribution or use, such as a bottle, vial, or syringe.

As used in the present disclosure, the term "vaporized chemical" refers to a chemical that has been converted into a substance that may be diffused or suspended in air. In some instances, a vaporized chemical may be a chemical that has been combined with water and then converted into a substance that may be diffused or suspended in air.

As used in the present disclosure, the term "fluid" refers to a liquid, semi-liquid, vapor, or gas including oxygen, hydrogen, nitrogen, or a combination thereof.

Embodiments of the present disclosure relate to systems and methods for the application of vaporized chemicals in the sterilization of medical products. For example, embodiments of the present disclosure may relate to systems and methods for the terminal sterilization of medical products using vaporized hydrogen peroxide (VHP). More particularly, embodiments of the present disclosure may relate to, e.g., systems and methods for the terminal sterilization of medical products, such as pre-filled syringes (PFS).

It is generally desired that exposure to sterilization cycles have no adverse impact and minimized risk of damage or alteration to products being sterilized. Medical products that undergo terminal sterilization, such as PFS, may thus require sterilization equipment, machinery, controls, cycle, and methods to conform to certain constraints and requirements in order to achieve appropriate sterilization and/or avoid damage to the medical products and/or devices, formulated drug substances, drug products, or other products. Such constraints and requirements may include, e.g.:

The medical products and/or surrounding packaging may be sensitive to deep vacuum pressures during the sterilization cycle. For example, PFS may include pre-positioned plungers susceptible to becoming dislodged when exposed to deep vacuum environments. Additionally, medical products may include fragile materials, such as glass, which may be affected by deep vacuum environments.

The medical products, compositions contained in medical products, and/or surrounding environment may be adversely affected by extreme temperatures during sterilization cycle. For example, products containing liquid formulations (e.g., liquid medicaments in PFS) may not be stable when heated to the higher temperatures to which they may be exposed during typical sterilization cycles. For example, medicaments in such liquid formulations may become denatured, deactivated, or otherwise altered when exposed to and/or heated to high temperatures.

Medical products may be densely packed; e.g., bulk packaged medical products may contain a large sum of fully assembled, packaged, and labeled medical products. In the case of terminal sterilization, sterilizing agents may need to traverse several layers of packaging materials, container materials, and/or labels.

In the case of some types of sterilization, such as terminal sterilization, sterilizing agents may need to traverse a semi-permeable membrane, either by heat or by mass, to sterilize the exterior of each medical product as well as the interior of packaging elements.

Packaging for medical products may resist penetration of sterilization materials, and/or may be sensitive to temperature and pressure changes caused by sterilization. For example, a syringe may be packaged in a plastic 'blister' configured to house the syringe and restrict it from movement. Such a blister may be only somewhat permeable to sterilization materials, and/or may be sensitive to changes in pressure.

Medical products may be sealed using temperature- or pressure-sensitive elements. For example, PFS may be sealed using a semi-permeable gas membrane 'lidding.'

Chemical sterilization, including moist chemical sterilization, may provide advantages addressing some of the above-described characteristics of medical product sterilization. For example, sterilization using a combination of VHP and vaporized water may advantageously be performed at relatively low temperatures, negating the need to expose medical products to disruptive high temperatures. However, there is limited evidence demonstrating successful application of VHP sterilization technology for terminal sterilization (e.g., for terminal sterilization of PFS), due to, e.g., sterilization cycles achieving incomplete sterilization, sterilization cycles unable to operate within allowable temperature and/or pressure ranges for medical products, difficulties in removing toxic residual VHP from sterilized articles, and/or long sterilization times. Ethylene oxide ("EtO") is a viable alternative to VHP, and is known to be an effective agent for sterilization of items sensitive to high temperatures and pressures. However, EtO is more toxic to humans than VHP, and as such presents health and safety issues during and after its use in a sterilization system.

For at least the above reasons, it may be desirable to more successfully apply VHP in terminal sterilization of medical products. It may also be desirable to do so while achieving relative sterilization "cycle efficiency" (e.g., (1) a decrease in overall sterilization cycle time, and/or (2) a decrease in extremity of the temperature at which a sterilization cycle operates). There is potentially significant value associated with successful application of VHP in terminal sterilization (e.g., of PFS), as well as improving cycle efficiency while applying VHP in terminal sterilization of PFS. The potential value may be derived by minimizing risk to product, and to business, by allowing more overall throughput of medical products (e.g., PFS) per unit of time.

Several aspects of VHP sterilization may (positively or negatively) affect the safety, efficacy, efficiency, and other aspects of sterilization processes for medical products. For example:

Vaporized sterilizing chemicals, such as VHP, may be stored as aqueous liquid mixtures, may be vaporized in the presence of water, and/or may otherwise exist in environments with water vapor. Under some sterilization conditions, vaporized sterilizing chemicals may not behave as a dry and/or ideal gas. VHP, for example, may not fully dissociate from water vapor in a sterilization chamber; the VHP may instead behave as a binary mixture of VHP and water vapor.

During some or all of a sterilization cycle, chemical sterilant vapors and water vapors in a sterilization chamber may adsorb to and/or condense on surfaces having cooler temperatures than the environmental temperature in the sterilization chamber. For example, during vapor sterilization of PFS loads, "cold spots" created by aqueous, high heat capacity, liquid product in each PFS, may serve to attract vapor adsorption and promote surface condensation. Upon proximity to a surface, chemical sterilant vapors and water vapors may adsorb to the surfaces due to the chemical properties of the vapors themselves, the operating conditions inside the chamber during sterilization, and the cooler temperatures on the surfaces of the PFS load as compared to the rest of the chamber environment.

During some or all of a sterilization cycle, VHP may preferentially adsorb onto surfaces as compared to water vapor, due to the fact that hydrogen peroxide is more dense and less volatile than water. In some instances, VHP and water vapor may be adsorbing and condensing on surfaces at the same time, with VHP adsorbing and condensing in greater quantities and percentages as compared to the water vapor, and in closer proximity to the surfaces of the sterilization load than the water vapor.

During some or all of a sterilization cycle, multiple layers of adsorption may form on the surfaces of PFS loads. In some instances, each layer of adsorption and/or condensation further away from the surface may contain less VHP and more water vapor, such that a gradient of VHP to water is formed on the surface. VHP may preferentially adsorb and condense closer to the surfaces of the load because of the thermodynamic behavior of binary mixtures of VHP and water vapor close to or at saturation (vapor/liquid equilibrium). Vapor/liquid equilibrium may be analogous to gas/adsorbate equilibrium for binary mixtures of VHP and water vapor in sterilization applications.

During or after a VHP sterilization cycle, condensed/adsorbed hydrogen peroxide may be difficult to remove from surfaces that it has sterilized, due in part to the condensation of water vapor over, and adsorption of water around, the condensed hydrogen peroxide, which may trap the hydrogen peroxide in place on the sterilized surfaces.

Systems and methods disclosed herein may advantageously be used in successfully sterilizing medical products, while decreasing the impact and/or risk of the sterilization process on the products undergoing sterilization. For example, systems and methods disclosed herein may provide for full (e.g., 100%) sterilization of medical products using VHP, followed by full (e.g., 100%) removal of VHP from sterilized products. Systems and methods disclosed herein may, e.g., increase efficiency, safety, and efficacy of sterilization, and/or decrease sterilization cycle time. Additionally, while aspects of the present disclosure may be described with respect to the use of VHP in terminal sterilization of PFS, sterilization of other medical products is contemplated by the present disclosure as well.

The present disclosure also contemplates performance of "moist chemical sterilization," by which chemical sterilization may be achieved in the presence of water vapor. Comparison of "moist chemical sterilization" to "chemical sterilization" may be analogous, in some cases, to comparison of "moist heat sterilization" to "heat sterilization." In some instances, moist chemical sterilization may be a more effective and efficient means of achieving sterilization than chemical sterilization technology that currently exists, in the same way that "moist heat sterilization" is considered to be, in some cases, more effective and efficient than only "heat sterilization."

"Moist chemical sterilization" may take place when environmental conditions of relatively high chemical concentration, high water vapor concentration, and high pressure (e.g., above 400 mbar) act in concert to force the chemical and water vapor to behave as a binary mixture. In order to achieve the desired relatively high chemical concentration, high water vapor concentration, and high pressure, the sterilization chamber (e.g., sterilization chamber 102) may be saturated with a combination of water vapor and sterilizing chemical (e.g., VHP), forcing vapor to condense on surfaces of the "load" or item or items to be sterilized (e.g., products 105). Most commercially available hydrogen peroxide is available and sold as aqueous liquid mixtures in varying concentrations (e.g., 3%, 15%, 35%, 59%), and thus, vaporizing hydrogen peroxide will generally simultaneously include vaporizing water. When VHP is used, because VHP has a higher density than water vapor, VHP may preferentially condense on the surfaces of the item or items to be sterilized over water vapor.

It is recognized herein that a portion of a sterilization load having a lower temperature than the surrounding sterilization environment (e.g., the ambient temperature of sterilization chamber 102), may act as a "cold spot" that attracts vapor to condense on the surface area of the load. If specific "cold spots" within the load are located inside packages which require vapor to travel through a semi-permeable membrane, these "cold spots" can advantageously attract condensation of vaporized VHP to the surface area surrounding the "cold spots," thus creating a higher density of condensed VHP in areas of the load and promoting diffusion of the sterilizing chemical through semi-permeable membranes that it contacts. On the other hand, it is recognized that if "cold spots" are too cold, that is, if there is too much of a temperature difference (delta) between the load or portions of the load and the surrounding sterilization environment (e.g., the temperature of sterilization chamber 102), the presence of the "cold spots" may prevent distribution and penetration of VHP over the entire load. Thus, it is recognized that a balanced temperature differential between the temperature of the sterilization environment (e.g., sterilization chamber 102) and the temperature of "cold spots" on items to be sterilized (e.g., products 105) is required, such that VHP is drawn to condense at "cold spots," but not to the detriment of diffusion over the load as a while.

Referring now to the figures, FIG. 1 depicts in schematic form an exemplary sterilization system 100. Sterilization system 100 includes a sterilization chamber 102, surrounded by a temperature control jacket 104. Sterilization chamber 102 has an interior cavity, including an upper interior 101 and a lower interior 103. Sterilization chamber 102 is configured to house one or more products 105 for sterilization. An inlet conduit 134, fluidly connected to sterilization chamber 102, is configured to allow various fluids to enter sterilization chamber 102 via a distribution manifold 107 in sterilization chamber 102. A second inlet conduit 135 is also fluidly connected to sterilization chamber 102, also to allow fluids to enter sterilization chamber 102 via an inlet 109. A blower 106 is fluidly connected to sterilization chamber 102 via a blower exit conduit 108. A blower circulation conduit 118 fluidly connects blower 106 to move fluids from blower exit conduit 108 either towards an exhaust 116, or back towards sterilization chamber 102 via inlet conduit 134. An exhaust valve 120 is located between blower circulation conduit 118 and exhaust 116, and selectively closes or opens a connection between blower circulation conduit 118 and exhaust 116. A recirculation valve 119 is located between blower circulation conduit and inlet conduit 134, and selectively closes or opens a connection between blower circulation conduit 118 and inlet conduit 134. A vacuum pump 110 is also fluidly connected to sterilization chamber 102, via a vacuum conduit 112 and a catalytic converter 115. A vacuum valve 113 is located on vacuum conduit 112, and selectively allows, partially allows, or blocks flow from sterilization chamber 102 through catalytic converter 115 and vacuum pump 110. A vacuum exhaust conduit 114 fluidly connects vacuum pump 110 to exhaust 116.

Several fluid supplies are also fluidly connected to sterilization chamber 102 via inlet conduit 134 or inlet conduit 135. An air supply 117 is configured to supply air to sterilization chamber 102 via inlet conduit 134. An air valve 124 is coupled to the fluid connection between air supply 117 and inlet conduit 134, and selectively allows, partially allows, or blocks flow of air from air supply 117 to sterilization chamber 102 via inlet conduit 134. Further, a VHP injector 132, fluidly connected to inlet conduit 134, is configured to inject VHP to sterilization chamber 102 via inlet conduit 134. A VHP injector valve 128 is coupled to the fluid connection between VHP injector 132 and inlet conduit 134, and selectively allows, partially allows, or blocks flow of VHP from VHP injector 132 to sterilization chamber 102 via inlet conduit 134. Additionally, a dry air supply 130 fluidly connected to inlet conduit 135 is configured to supply dry air to sterilization chamber 102 via inlet conduit 135. A dry air supply valve 126 is coupled to the fluid connection between dry air supply 130 and inlet conduit 135, and is configured to selectively allow, partially allow, or block flow of dry air from dry air supply 130 to sterilization chamber 102 via inlet conduit 134. A controller 140 is connected to one or more other components of sterilization system 100, such as sterilization chamber 102, temperature control jacket 104, blower 106, VHP injector 132, air supply 117, dry air supply 130, and/or any other components of sterilization system 100.

Sterilization system 100 may be configured to run sterilization cycles within sterilization chamber 102 at a variety of temperatures and pressures, and for a variety of time durations and/or time intervals. In some embodiments, the temperature(s), pressure(s), and time interval(s) at which sterilization system 100 may run sterilization cycles may be selectively and individually modified and customized. Sterilization system 100 may be configured to control the environment in the interior of sterilization chamber 102, including temperature, pressure, humidity, atmosphere, intake of fluids via, e.g., inlet conduit 134, exit of fluids via one or more of temperature or pressure controls, and/or via e.g., blower exit conduit 108 and/or vacuum conduit 112. Further, sterilization system 100 may include any suitable number and location of sensors configured to sense, e.g., temperature, pressure, flow, chemical concentration, or other parameters throughout sterilization system 100, including in sterilization chamber 102, temperature control jacket 104, blower 106, vacuum pump 110, and/or any of conduits 108, 112, 114, 118, and 134. Such sensors may be configured to transmit sensed data to, e.g., controller 140 and/or a human-machine interface.

Sterilization chamber 102 may be a sealable chamber defining an interior, including upper interior 101 and lower interior 103. Sterilization chamber 102 may be openable into an open configuration, such that one or more items, e.g., products 105, may be placed inside as a part of a load for sterilization, and may be removed subsequent to sterilization. In some embodiments, sterilization chamber 102 may have an operating orientation, e.g., such that upper interior 101 is located above lower interior 103, and such that matter may fall (e.g., under the forces of gravity) from the vicinity of upper interior 101 towards lower interior 103. Sterilization chamber 102 may have one or more delivery apparatus to which one or more of inlet conduit 134 and inlet conduit 135 may be connected. As depicted in FIG. 1, for example, distribution manifold 107 is one such delivery apparatus. Distribution manifold 107 may be configured to disperse gas, vapor, or liquid into sterilization chamber 102 in a given configuration, such as a stream or an even spray across upper interior 101 of sterilization chamber 102. Inlet 109 is another such delivery apparatus. Inlet 109 may also be configured to disperse gas, vapor, or liquid into sterilization chamber 102 in a given configuration, such as a stream, or an even spray across upper interior 101. In some embodiments, distribution manifold 107 may be configured to disperse gas, vapor, or liquid into sterilization chamber 102 in one configuration, such as an even spray, and inlet 109 may be configured to disperse gas or vapor into sterilization chamber 102 in a different configuration, such as in a stream. In some embodiments, there may be no inlet 109, and both inlet conduits 134 and 135 may be connected to distribution manifold 107.

Temperature control jacket 104 may be any material surrounding sterilization chamber 102, that is configured or effective to afford temperature control to the environment inside sterilization chamber 102. In some embodiments, for example, temperature control jacket 104 may be a water jacket surrounding sterilization chamber 102. In such embodiments, a temperature and/or a flow of water or other liquid through temperature control jacket 104 may be controlled by, e.g. controller 140.

Products 105 may be any item or items suitable for sterilization using sterilization system 100. In some embodiments, products 105 may be medical products in primary packaging, secondary packaging, or both. In some embodiments, products 105 may be medical products having moving parts or parts otherwise sensitive to deep vacuum environments, such as environments having pressure of less than about 100 millibars. Products 105, therefore, may be, e.g., containers filled with a volume of formulated drug substance, such as, e.g., vials or PFS. In further embodiments, products 105 may be or include medical products sensitive to high temperatures, e.g., above 30° C. Such medical products may include, for example, formulated drug substances or other compositions that may be sensitive to high temperatures, such as proteins (e.g., antibodies or enzymes), nucleic acids, blood, blood components, vaccines, allergenics, gene therapy medicaments, tissues, other biologics, etc. For example, products 105 may be packaged PFS containing a formulated drug substance that includes an antibody.

Blower 106 may be, for example, a blower having the capacity to forcibly draw vapor and gas from lower interior 103 of sterilization chamber 102 through blower exit conduit 108, and to reintroduce said vapor and gas back to upper interior 101 of sterilization chamber 102 via inlet conduit 134 (or, alternatively, to draw such vapor and gas through exhaust valve 120 and catalytic converter 121, to exhaust 116). Blower 106 may be any device or mechanism configured or effective to perform this function. For example, blower 106 may have an impeller and rotating blades, or rotating vanes configured to draw vapor and gas from lower interior 103 out of blower exit conduit 108, through blower circulation conduit 118, and back to upper interior 101 of sterilization chamber 102 via inlet conduit 134. In some embodiments, blower 106 may be external to sterilization chamber 102, as shown in FIG. 1. In other embodiments, blower 106 may be disposed within sterilization chamber 102. In some embodiments, blower 106 may be configured to draw vapor and gas from lower interior 103 of sterilization chamber 102 and reintroduce said vapor and gas back to upper interior 101 with sufficient force to create a flow of vapor and gas from upper interior 101 to lower interior 103 of sterilization chamber 102. This flow may be termed a "turbulent flow." In some embodiments, the force with which blower 106 may operate may be adjustable (via, for example, controller 140), such that a more turbulent (e.g., more forceful), or less turbulent, flow of vapor and gas within sterilization chamber 102 may be generated. In some embodiments, blower 106 may be configured to generate a stronger force to draw vapor and gas than, e.g., vacuum pump 110.

Vacuum pump 110 may be a vacuum pump having the capacity to draw gas from the interior (e.g., lower interior 103) of sterilization chamber 102, via vacuum conduit 112 and catalytic converter 115, and towards exhaust 116, thereby creating a vacuum within sterilization chamber 102 and/or a closed system containing sterilization chamber 102 and, e.g., blower 106. In some embodiments, vacuum pump 110 may have an impeller, rotating blades, or vanes configured to draw vapor and gas towards exhaust 116. Vacuum pump 110 may be fluidly connected to exhaust 116 via, e.g., vacuum exhaust conduit 114. In some embodiments, exhausts from vacuum pump 110 and blower 106 may be separated instead of being combined into one.

In some embodiments, vacuum-type functions may also or alternately be performed by, e.g., blower 106, which may selectively circulate vapor and gas out of and into sterilization chamber 102 or out of sterilization chamber 102, through exhaust valve 120, and towards exhaust 116. Exhaust valve 120 may be selectively opened or closed so as to permit or prevent flow of gas or vapor from blower circulation conduit 118 towards exhaust 116 or towards inlet conduit 134 for reintroduction into sterilization chamber 102. Exhaust valve 120 may be manually controlled, or may be controlled by, e.g., controller 140.

Sterilization system 100 may include several supplies of air and/or vapor from which fluid may be introduced into sterilization chamber 102 via inlet conduit 134 or inlet conduit 135. Air supply 117, for example, may be any supply of air (e.g., room air, or compressed dry air) or other fluid external from the rest of sterilization system 100. In some embodiments, air supply 117 may be a supply of "room air" surrounding sterilization system 100, which may have gone through an indoor filtration system. In some embodiments, air supply 117 may include more water vapor than "room air." In some embodiments, air supply 117 may be a supply of filtered outdoor air. Air valve 124, coupled to the fluid connection between air supply 117 and inlet conduit 134, may be configured to selectively allow, partially allow, or block flow of air from air supply 117 to sterilization chamber 102 via inlet conduit 134, thus controlling the intake of air into closed portions of sterilization system 100. Air valve 124 may be manually controllable and/or controllable by, e.g., controller 140.

Dry air supply 130 may be a supply of air having a relatively low humidity, such that it may be used to dry the interior of, e.g., sterilization chamber 102 and/or one or more of conduits 108, 112, 114, 118, and 134. In some embodiments, for example, air in dry air supply 130 may include a dew point of, e.g., −10 degrees Celsius or less, −40 degrees Celsius or less, or anywhere between −10 degrees Celsius and −40 degrees Celsius. In some embodiments, dry air supply 130 may be a supply of hygienic dry air, such as air that has been sterilized or otherwise filtered to at least 0.2 microns. In some embodiments, dry air supply 130 may be a sealed supply of air. In some embodiments, dry air supply 130 may be a supply of compressed air. Dry air supply valve 126, coupled to the fluid connection between dry air supply 130 and inlet conduit 135, may be configured to selectively allow, partially allow, or block flow of dry air from dry air supply 130 to sterilization chamber 102 via inlet conduit 135. Dry air supply valve 126 may be manually controllable and/or may be controllable by, e.g., controller 140. In some embodiments, dry air supply 130 may be connected to inlet conduit 134 instead of inlet conduit 135. In further embodiments, air supply 117 may supply any of the types of air that dry air supply 130 includes.

VHP injector 132 may include a supply of VHP, or VHP and vaporized water, and may be configured to inject VHP or a combination of VHP and vaporized water into sterilization chamber 102 via, e.g., inlet conduit 134. VHP injector 132 may be configured to inject vapor into sterilization chamber 102 at an adjustable concentration. VHP injector valve 128 may be coupled to the fluid connection between VHP injector 132 and inlet conduit 134, and may be configured to selectively allow or block flow of VHP from VHP injector 132 to sterilization chamber 102 via inlet conduit 134. VHP injector valve 128 may be manually controllable and/or may be controllable by, e.g., controller 140. Dry air supply valve 126 and VHP injector valve 128 may also be used in concert to allow a desired combination of dry air and vaporized VHP/water into sterilization chamber 102, via inlet conduit 134.

Catalytic converter 115 and catalytic converter 121 may be, for example, any catalytic converters known in the art suitable for converting toxic gaseous or vaporized fluids circulated within sterilization system 100, e.g., during a sterilization cycle, to less toxic gases or vapors. For example, catalytic converters 115, 121 may be configured to convert VHP injected into sterilization system 100 by VHP injector 132 into water vapor, oxygen, or other non-toxic fluids.

Some or all aspects of sterilization system 100 may be controllable by, e.g., controller 140. Controller 140 may be, for example, an analog or digital controller configured to alter aspects of the environment of sterilization chamber 102 such as an internal temperature or pressure of sterilization chamber 102 and/or one or more of blower 106, vacuum pump 110, air supply 117, dry air supply 130, VHP injector 132, exhaust 116, one or more of valves 113, 119, 120, 124, 126, and 128, one or more of catalytic converters 115, 121, one or more of conduits 108, 112, 114, 116, 118, and 134, and any and/or other aspects of sterilization system 100. In some embodiments, sterilization system 100 may be controllable by multiple controllers 140. In other embodiments, sterilization system may only have one controller 140. In some embodiments, controller 140 may be a digital controller, such as a programmable logic controller.

In some embodiments, controller 140 may be pre-programmed to execute one or more sterilization cycles using sterilization system 100. In some embodiments, sterilization system 100 may be controllable by a controller having one or more human machine interface ("HMI") elements, which may be configured to allow a user to input or alter desired parameters for a sterilization cycle, which may be executable by a controller on or operably coupled to sterilization system 100. Thus, in some embodiments, HMI elements may be used to program a customized sterilization cycle for execution by sterilization system 100. For example, in some embodiments, sterilization system 100 may be controllable by a controller connected to, e.g., a computer, tablet, or handheld device having a display. Such a display may include, for example, options to select or alter a desired temperature, pressure, time, amount of VHP intake, etc., for one or more steps of a sterilization cycle.

FIGS. 2 and 3A-3C depict flow diagrams of phases and steps in methods for sterilization according to the present disclosure. As will be recognized by one of ordinary skill in the art, some phases and/or steps in FIGS. 2 and 3A-3C may be omitted, combined, and/or performed out of order while remaining consistent with the present disclosure. In some embodiments, the phases and steps in FIGS. 2 and 3A-3C may be performed using, e.g., sterilization system 100 or a variation of sterilization system 100. It will be recognized that the customizable and controllable aspects of sterilization system 100 may be used in order to carry out phases and steps depicted in FIGS. 2 and 3A-3C. For example, in some embodiments, controller 140 may be employed to direct, adjust, or modify a series of sterilization steps, setpoints, and phases performable by sterilization system 100. Additionally, although the phases and steps described in FIGS. 2 and 3A-3C are recited in relation to sterilization system 100, one of ordinary skill in the art will understand that these phases and steps may be performed by another sterilization system, or another system having the capacity to carry out the steps.

FIG. 2 depicts a flow diagram of a series of steps in a method 200 for sterilization according to the present disclosure in a sterilization system, such as sterilization system 100. According to step 202, a leak test may be performed on sterilization system 100. According to step 204, sterilization system 100 may be preconditioned. According to step 206, a sterilization phase may be performed. According to step 208, a first aeration phase may be performed. According to step 208, a second aeration phase may be performed.

Prior to performance of the steps of method 200, a sterilization load, such as products 105, may be placed within a sterilization chamber, such as sterilization chamber 102, of a sterilization system, such as sterilization system 100. The closed-system sterilization environment—including sterilization chamber 102, blower exit conduit 108, blower 106, blower circulation conduit 118, inlet conduit 134, and any elements connecting these components—may then be sealed.

According to step 202, a leak test may be performed on the closed-system sterilization environment. The leak test may include, for example, creating a vacuum through the closed system. The vacuum may be created by, e.g., expelling gas and vapor from the closed system using vacuum pump 110. During the leak test, blower 106 may be in operation, so as to circulate any remaining air through the closed system and create a homogenous environment. The leak test may be performed in this manner in part to verify that a suitable vacuum may be held within the closed system. Additionally, inclusion of, and circulation of air through, the entirety of the closed system in the leak test may assist in increasing the heat transfer coefficient between the environment within the closed system and the load to be sterilized, which may assist in equalizing the temperature between the environment within the closed system and the load to be sterilized prior to sterilization.

According to step 204, the sterilization system (e.g., sterilization system 100) may be preconditioned. Preconditioning may include, for example, increasing the temperature of the closed system to temperatures intended to be maintained during a sterilization phase (e.g., between about 25° C. and about 50° C.). In some embodiments, preconditioning may be performed for longer than is performed in standard chemical sterilization procedures, which may allow more time for any temperature difference between the environment in the closed system (including, e.g., the environment of sterilization chamber 102) and the load to be sterilized to decrease. In some embodiments, preconditioning may be performed for between about 15 minutes and about two hours, such as between about 20 minutes and about 1.5 hours, between about 25 minutes and about 1 hour, between about 30 minutes and about 1 hour, between about 30 minutes and about 45 minutes, between about 45 minutes and about 1 hour, such as about 30 minutes, about 40 minutes, about 45 minutes, or about 1 hour. Preconditioning according to step 204 also may include operating at pressures which are at or near atmospheric pressure, e.g., between about 400 millibars and about 700 millibars, between about 500 millibars and about 700 millibars, between about 500 millibars and about 600 millibars, between about 800 millibars and about 1000 millibars, or between about 900 millibars and about 1100 millibars. Operation of the preconditioning step at or near atmospheric pressure may promote convective heat transfer from the chamber environment to the load, assisting in minimizing the difference in temperature between the chamber environment and the load. Additionally, blower 106 may be operated during preconditioning according to step 204, which may contribute to a higher heat transfer coefficient, and thus potentially faster equalization of temperature between the closed system, including the environment of sterilization chamber 102, and the load to be sterilized. Equalization of temperature between the closed system and the load to be sterilized may allow for warming of "cold spots," or locations on or in the load having a cooler temperature than the majority of the load and/or the surrounding environment. For example, liquid contents of PFS may absorb heat more slowly than their non-liquid packaging, thus acting as "cold spots" within a load containing the PFS. Reduction of such cold spots by equalizing the temperature throughout the closed system and the load to be sterilized may advantageously allow for even diffusion of a vaporized sterilizing chemical (e.g., VHP) through sterilization chamber 102, across the load to be sterilized, and/or diffusion through permeable membranes and barriers in the load to be sterilized. Maintaining some temperature difference between the closed system and the "cold spots" may be desirable, however, to promote preferential surface adsorption and condensation of VHP and water vapor onto the load to be sterilized.

As is discussed elsewhere herein, it is also contemplated that, in some embodiments, maintaining "cold spots" via keeping a temperature differential between the load to be sterilized and the surrounding closed system may also have advantages; for example, controlled condensation of vaporized sterilizing chemical (e.g., VHP) on "cold spots" of a load to be sterilized may concentrate the sterilizing chemical on the load and lead to more efficient diffusion of the chemical into the load, thus decreasing the overall amount of sterilizing chemical needed in the sterilization chamber 102 to achieve effective sterilization. In such embodiments, preconditioning according to step 204 may be performed for a shorter amount of time and/or in a shallow vacuum created by, e.g., vacuum pump 110, in order to allow for or maintain "cold spots" within the load to be sterilized.

According to step 206, a sterilization phase may be performed. The sterilization phase may include, for example, initiating circulation of fluid through the sterilization system, achieving a vacuum level, injecting vaporized chemical into the sterilization chamber, maintaining a post-injection hold, injecting gas into the sterilization chamber to transition to a shallower vacuum, and maintaining a post-transition hold. The sterilization phase according to step 206 may be repeated multiple times. A sterilization phase according to step 206 is depicted in further detail in FIG. 3A.

According to step 208, a first aeration phase may be performed. The first aeration phase may include, for example, achieving a vacuum level, holding the vacuum level, breaking the vacuum level, and aerating and exhausting the system. The first aeration phase may be performed multiple times. A first aeration phase according to step 208 is depicted in further detail in FIG. 3B.

According to step 210, a second aeration phase may be performed. The second aeration phase may include, for example, achieving a vacuum level, holding the vacuum level, and breaking the vacuum level. The second aeration phase may be performed multiple times. A second aeration phase according to step 210 is depicted in further detail in FIG. 3C.

Both steps 208 and 210 may be performed multiple times. Additionally, while in some embodiments, step 208 may be performed before step 210, in alternative embodiments, step 210 may be performed before step 208.

Figure 3A:
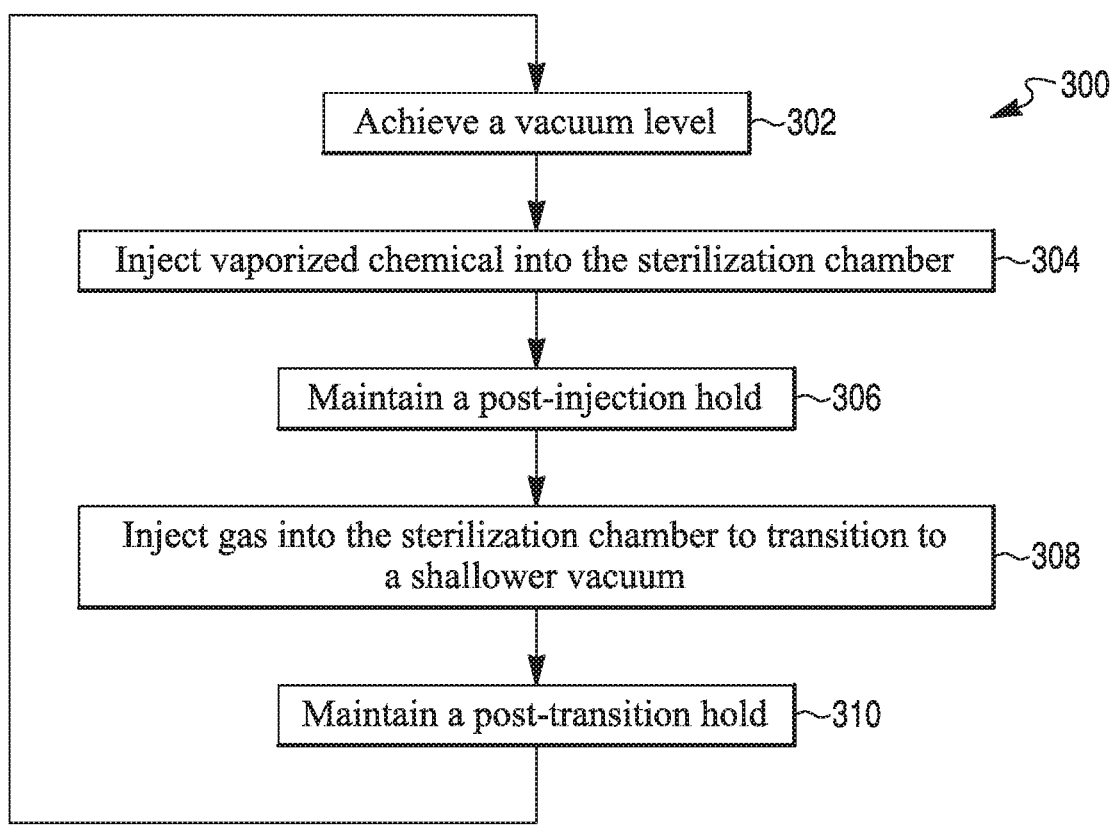
FIGS. 3A-3C are additional flow diagrams of steps in an exemplary method of sterilizing medical products using vaporized chemicals.

FIG. 3A is a flow diagram of a sterilization phase 300 that may be performed as step 206 of sterilization method 200. Prior to sterilization phase 300, a sterilization load (e.g., products 105) may be introduced into sterilization chamber 102. According to step 302, a vacuum level may be achieved. According to step 304, vaporized chemical may be injected into the sterilization chamber. According to step 306, a post-injection hold may be maintained. According to step 308, gas may be injected into the sterilization chamber to transition to a shallower vacuum. According to step 310, a post-injection hold may be maintained.

As a part of sterilization phase 300, a turbulent flow may be initiated and maintained in sterilization system 100.

According to step 302, a vacuum level may be achieved within sterilization chamber 102 of sterilization system 100. The vacuum level may be, for example, between about 400 millibars and about 700 millibars, such as between about 450 millibars and about 650 millibars, or between about 450 millibars and about 550 millibars. For example, the vacuum may be about 450 millibars, about 500 millibars, about 550 millibars, or about 600 millibars. This vacuum may promote a higher concentration of sterilizing chemical on the sterilization load, extending the amount of time at which the closed system is kept at a deeper vacuum increases exposure of the sterilization load to the sterilizing chemical.

According to step 304, vaporized chemical may be injected into the sterilization chamber. In some embodiments, the vaporized chemical may include VHP. In some embodiments, the vaporized sterilization chemical may be a vaporized aqueous hydrogen peroxide solution, having a concentration of, for example, between about 5% and about 75% hydrogen peroxide by weight. In some embodiments, the vaporized chemical may be a vaporized aqueous hydrogen peroxide solution having a concentration of, for example, between about 10% and about 65% hydrogen peroxide by weight, between about 15% and about 60% hydrogen peroxide by weight, between about 30% and about 60% hydrogen peroxide by weight, between about 30% and about 60% hydrogen peroxide by weight, or between about 45% and about 60% hydrogen peroxide by weight. In some embodiments, the vaporized chemical may be a vaporized aqueous hydrogen peroxide having a concentration of about 35% hydrogen peroxide (and 65% water) by weight. In further embodiments, the vaporized chemical may be a vaporized aqueous hydrogen peroxide having a concentration of about 59% hydrogen peroxide (and 41% water) by weight.

In some embodiments, an injected supply of VHP may be, for example, between about 50 g and about 700 g of aqueous VHP. For example, the injected supply of VHP may be between about 50 g and about 600 g, between about 100 g and about 600 g, between about 300 g and about 550 g, or between about 450 g and about 550 g. For example, the injected supply of VHP may be about 100 g, about 200 g, about 300 g, about 400 g, about 450 g, about 475 g, about 500 g, about 525 g, about 550 g, about 600 g, or about 650 g. In some embodiments, an injected supply of VHP may be quantified based on the volume or amount of load to be sterilized inside sterilization chamber 102. For example, if a number of drug products, such as pre-filled syringes, are to be sterilized in sterilization chamber 102, an injected supply of VHP may be between about 0.01 and about 0.15 grams of VHP per unit of the drug product inside sterilization chamber 102, such as between about 0.01 and about 0.10 grams of VHP, such as about 0.015 grams, 0.02 grams, 0.025 grams, 0.03 grams, 0.04 grams, 0.05 grams, 0.06 grams, 0.07 grams, 0.08 grams, 0.09 grams, 0.1 grams, or 0.11 grams per drug product. In other embodiments, an injected supply of VHP may be quantified based on the volume of the sterilization environment, such as the interior of sterilization chamber 102. For example, an injected supply of VHP may be between about 0.2 and 3.0 grams per cubic foot of volume in a sterilization chamber. For example, an injected supply of VHP may be between about 0.2 and about 2.0 grams per cubic foot, such as about 0.25 grams, about 0.50 grams, about 0.75 grams, about 1.0 gram, about 1.2 grams, about 1.4 grams, about 1.5 grams, about 1.6 grams, about 1.8 grams, or about 2.0 grams per cubic foot.

In some embodiments, step 210 may also include injecting dry air from, e.g., dry air supply 130, into the sterilization system, so as to create a desired balance between concentrations of vaporized chemical and water vapor, at different pressures, inside the chamber.

According to step 306, a post-injection hold may be maintained. During the post-injection hold, turbulent flow is maintained through the closed system including sterilization chamber 102 and blower 106. No fluids are added or removed from the closed system in which the turbulent flow is maintained. The time for which a post-injection hold is maintained (or the "post-injection hold time") may be selected so as to allow the vaporized sterilization chemical adequate time to contact the load to be sterilized. In some embodiments, the post-injection hold time may be between about 2 minutes and about 20 minutes. In some embodiments, the post-injection hold time may be at least about 5 minutes, at least about 10 minutes, or at least about 15 minutes. In some embodiments, the post-injection hold time may be between about 5 minutes and about 20 minutes, between about 8 minutes and about 20 minutes, between about 10 minutes and about 20 minutes, or between about 10 minutes and about 15 minutes. In such a manner, the need for adding excess VHP into the system to ensure its contact with the sterilization load may be avoided.

According to step 308, gas may be injected into the sterilization chamber to transition to a shallower vacuum (i.e., a higher pressure) in the sterilization chamber. The gas may be any suitable gas that can break or lessen the vacuum in sterilization chamber 102. In some embodiments, the gas may be a dry gas, such as a gas containing nitrogen (e.g., commercially available supplies of only nitrogen or primarily nitrogen), or air having a dew point of, for example, −10° C. or colder. In some embodiments, gas may be injected from dry air supply 130. The gas may be injected in a volume to achieve a pressure between about 500 millibars and about 1100 millibars, such as between about 550 millibars and about 1000 millibars, between about 600 millibars and about 1000 millibars, between about 700 millibars and about 700 millibars and about 900 millibars, or between about 750 millibars and about 850 millibars. For example, the second post-injection pressure may be about 700 millibars, about 750 millibars, about 800 millibars, about 850 millibars, or about 900 millibars.

According to step 310, a post-transition hold may be maintained. During the post-transition hold, the pressure achieved during step 308 may be maintained for, for example, at least about 5 minutes, at least about 10 minutes, or at least about 15 minutes. In some embodiments, the second post-injection pressure may be maintained for between about 5 minutes and about 20 minutes, between about 8 minutes and about 20 minutes, between about 10 minutes and about 20 minutes, or between about 10 minutes and about 15 minutes.

The steps of sterilization phase 300 may be repeated, for example, between 1 and 10 times, such as 2, 3, 4, 5, 6, 7, 8, 9, or 10 times. This may aid in ensuring full sterilization of the sterilization load within sterilization chamber 102. In some embodiments, the number of times that sterilization phase 300 may be repeated may be inversely proportional to the time that the post-injection hold is maintained in each repetition. For example, if the time that the post-injection hold is maintained is short (e.g., 10 minutes), then steps 210 through 216 may be repeated a greater number of times. In some embodiments, the post-injection hold is maintained for a longer period of time (e.g., 15-20 minutes), to increase the time during which the sterilization load is exposed to the sterilizing chemical in each repetition of sterilization phase 300. In further embodiments, the number of times that sterilization phase 300 may be repeated may depend on a total desired amount of VHP for the sterilization process. In some embodiments, for example, injection of a total amount of at least 200 g of VHP may be desired. For example, in some embodiments, injection of a total amount of at least 250 g may be desired. In some embodiments, injection of a total amount of between about 200 g and about 700 g of VHP may be desired.

Figure 3B:
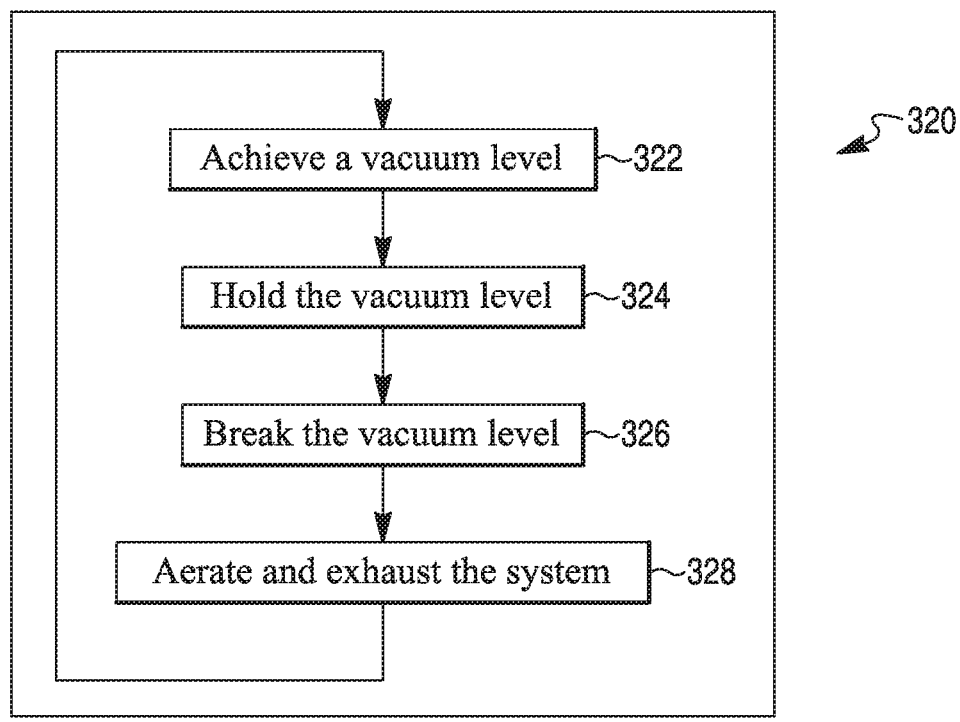

FIG. 3B is a flow diagram of a first aeration phase 320 that may be performed as step 208 of sterilization method 200, after performing one or more repetitions of sterilization phase according to step 206. According to step 322, a vacuum level may be achieved. According to step 324, the vacuum level may be held. According to step 326, the vacuum level may be broken. According to step 328, the sterilization system (e.g., sterilization system 100) may be aerated and exhausted.

According to step 322, a vacuum level may be achieved in sterilization chamber 102, while also injecting dry gas into sterilization chamber 102 near upper interior 101 of sterilization chamber 102, such as via distribution manifold 107 or inlet 109. The dry gas may include, for example, oxygen and/or nitrogen. The dry gas may have a dew point of, for example, −10° C. or lower. The dry gas may be injected from, e.g., dry air supply 130. While dry gas is being injected into sterilization chamber 102, a vacuum may be pulled by, e.g., vacuum pump 110 via vacuum conduit 112, catalytic converter 115, and vacuum exhaust conduit 114. The vacuum may be pulled at a greater rate than the rate of injection of dry gas, such that a vacuum level is gradually achieved. The vacuum level may be, for example, between about 500 millibars and about 850 millibars, such as between about 500 millibars and about 800 millibars, between about 550 millibars and about 750 millibars, or between about 600 millibars and about 700 millibars. For example, the vacuum level may be 500 millibars, 550 millibars, 600 millibars, 650 millibars, or 700 millibars. Injection of the dry gas near upper interior 101 of sterilization chamber 102 while achieving a desired vacuum level reduces condensation of VHP and water vapor at upper interior 101 of the chamber, and promotes the movement of denser molecules in sterilization chamber towards the lower interior (e.g., lower interior 103) of sterilization chamber 102, and to some extent out of sterilization system 100 through vacuum exhaust conduit 114.

According to step 324, injection of dry gas may be stopped and the vacuum level may be held for, e.g., between about 1 minute and about 20 minutes, such as between about 2 min and about 20 min, between about 5 min and about 20 min, between about 5 min and about 15 min, or between about 5 min and about 10 min. For example, the vacuum level may be maintained for about 2, 5, 8, 10, or 15 minutes. Holding the vacuum level may continue to promote settling of denser molecules (e.g., sterilization chemical molecules) down towards the lower interior 103 of sterilization chamber 102, and away from the sterilization load.

According to step 326, the vacuum level may be broken by the addition of more dry gas near upper interior 101 of sterilization chamber 102, via, for example, distribution manifold 107 or inlet 109. A volume of dry gas sufficient to achieve a higher pressure may be added. The higher pressure may be, for example, between 50 and 200 millibars higher than the vacuum level achieved in step 322. The vacuum level may be, for example, between about 550 millibars and about 1000 millibars, such as between about 550 millibars and about 850 millibars, between about 600 millibars and about 700 millibars, or between about 650 millibars and about 750 millibars. For example, the vacuum level may be about 550 millibars, 600 millibars, 650 millibars, 700 millibars, 750 millibars, or 800 millibars. The addition of more dry gas may continue to force sterilization chemicals to settle to the lower interior 101 of sterilization chamber 102, thus moving them away from the sterilization load and positioning them for removal via vacuum conduit 112 or blower exit conduit 108.

According to step 328, the sterilization system (e.g., sterilization system 100) may be aerated and exhausted. During this step, blower 106 may be turned on while recirculation valve 119 is closed and exhaust valve 120 is opened, such that blower 106 pulls fluid from within sterilization chamber 102 and expels it through exhaust 116 via catalytic converter 121. Because blower exit conduit 108 is connected to sterilization chamber 102 at lower interior 103 of sterilization chamber 102, denser fluids that have settled to lower interior 103 (such as sterilizing chemicals) may be removed by this step. Air (e.g., from air supply 117) may be concurrently allowed to vent into sterilization chamber 102, such that the pressure in sterilization chamber 102 returns to, or near, atmospheric pressure.

First aeration phase 320 may be repeated, for example, between 1 and 35 times, such as 2, 5, 10, 15, 17, 19, 22, 25, 27, 29, 30, 32, or 35 times. Repetition of first aeration phase 320 may ensure that the majority of sterilization chemical (e.g., VHP) is removed from sterilization system 100.

Figure 3C:
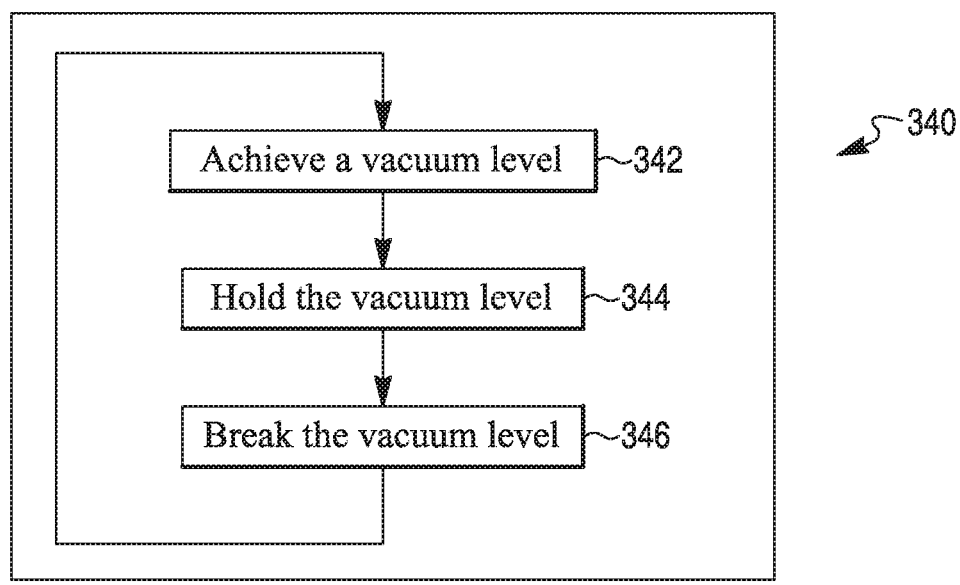

FIG. 3C is a flow diagram of a second aeration phase 340 that may be performed as step 210 of sterilization method 200. According to step 342, a vacuum level may be achieved. According to step 344, a vacuum level may be held. According to step 346, the vacuum level may be broken.

According to step 342, a vacuum level may be achieved in sterilization chamber 102. Like with the first aeration phase, the vacuum level achieved in this phase may be, for example, between about 500 millibars and about 850 millibars, such as between about 500 millibars and about 800 millibars, between about 550 millibars and about 750 millibars, or between about 600 millibars and about 700 millibars. For example, the vacuum level may be 500 millibars, 550 millibars, 600 millibars, 650 millibars, or 700 millibars. Achieving a vacuum level may promote removing of moisture from sterilization chamber 102 and thus the sterilization load. Thus, the sterilization load may be dried.

According to step 344, the vacuum level may be held for, e.g., between about 1 minute and about 20 minutes, such as between about 2 min and about 20 min, between about 5 min and about 20 min, between about 5 min and about 15 min, or between about 5 min and about 10 min. For example, the vacuum level may be maintained for about 2, 5, 8, 10, or 15 minutes. Holding the vacuum level may continue to promote removal of moisture from sterilization chamber 102, and thus the sterilization load. Thus, the sterilization load may be further dried. In some embodiments, step 344 may be omitted.

According to step 346, the vacuum level in sterilization chamber 102 may be broken, or raised to a higher pressure, by the addition of dry gas from, e.g., dry air supply 130.

Second aeration phase 340 may be repeated, for example, between 1 and 50 times, such as 2, 5, 10, 15, 20, 25, 30, 35, 38, 40, 42, 45, 47, 49, or 50 times. Repetition of second aeration phase 340 may ensure drying of sterilization chamber 102 and the sterilization load.

As has been previously described, second aeration phase 340 may be performed either before or after first aeration phase 320. First aeration phase 320 may ensure, for example, that the concentration of sterilizing chemical (e.g., VHP) in sterilization chamber 102 is relatively low, and second aeration phase 340 may ensure that the sterilization load is dried, and may also remove residual sterilizing chemical remaining in sterilization chamber 102 after first aeration phase 320. In cases where second aeration phase 340 is performed after first aeration phase 320, first aeration phase may ensure that the concentration of sterilization chemical (e.g., VHP) in sterilization chamber 102 is relatively low so that when sterilization chamber 102 and the sterilization load are dried in second aeration phase 340, there is little remaining need to remove residual sterilization chemical from the sterilization system 100.

Figure 4A:
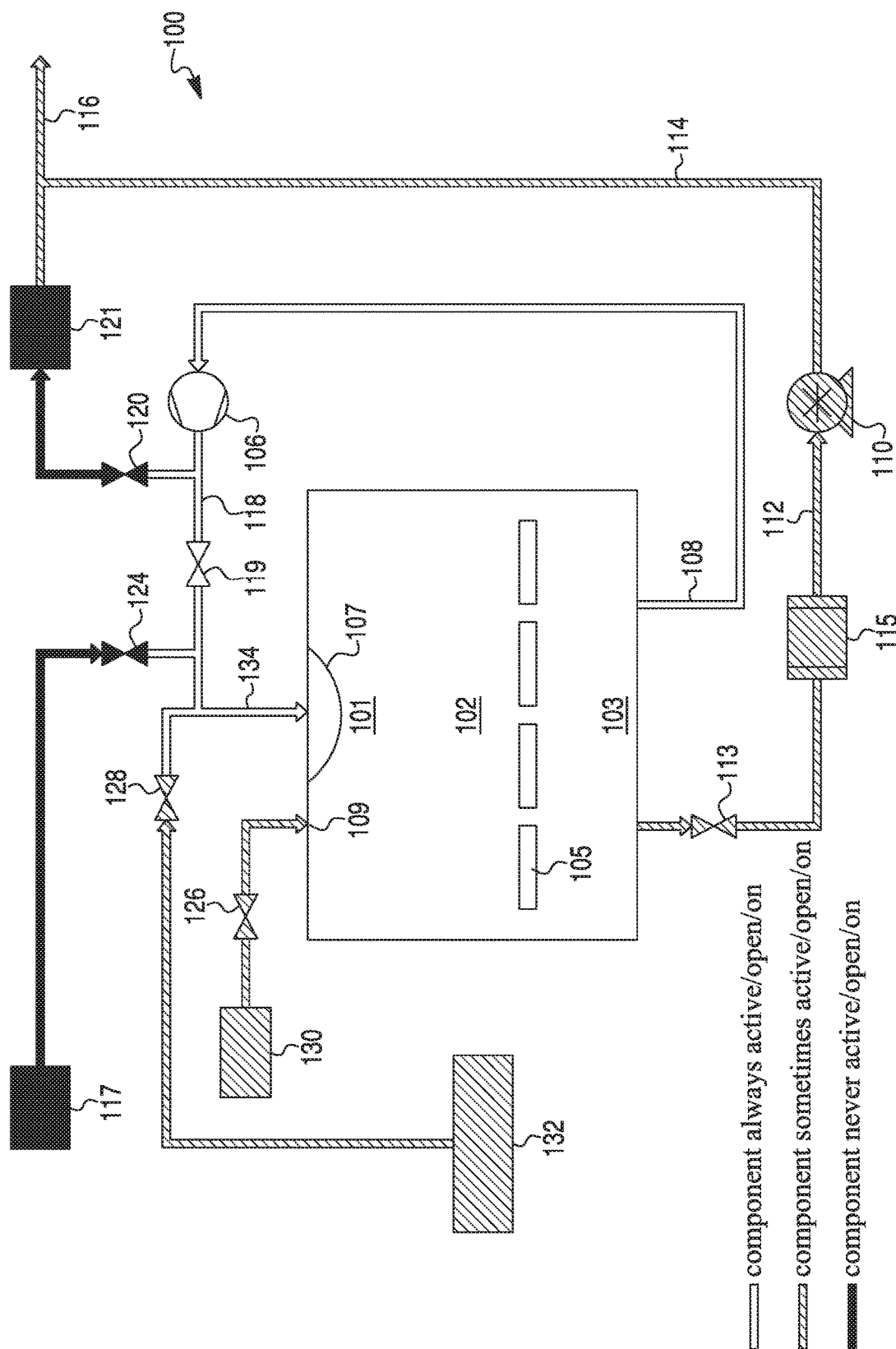
Figure 4B:
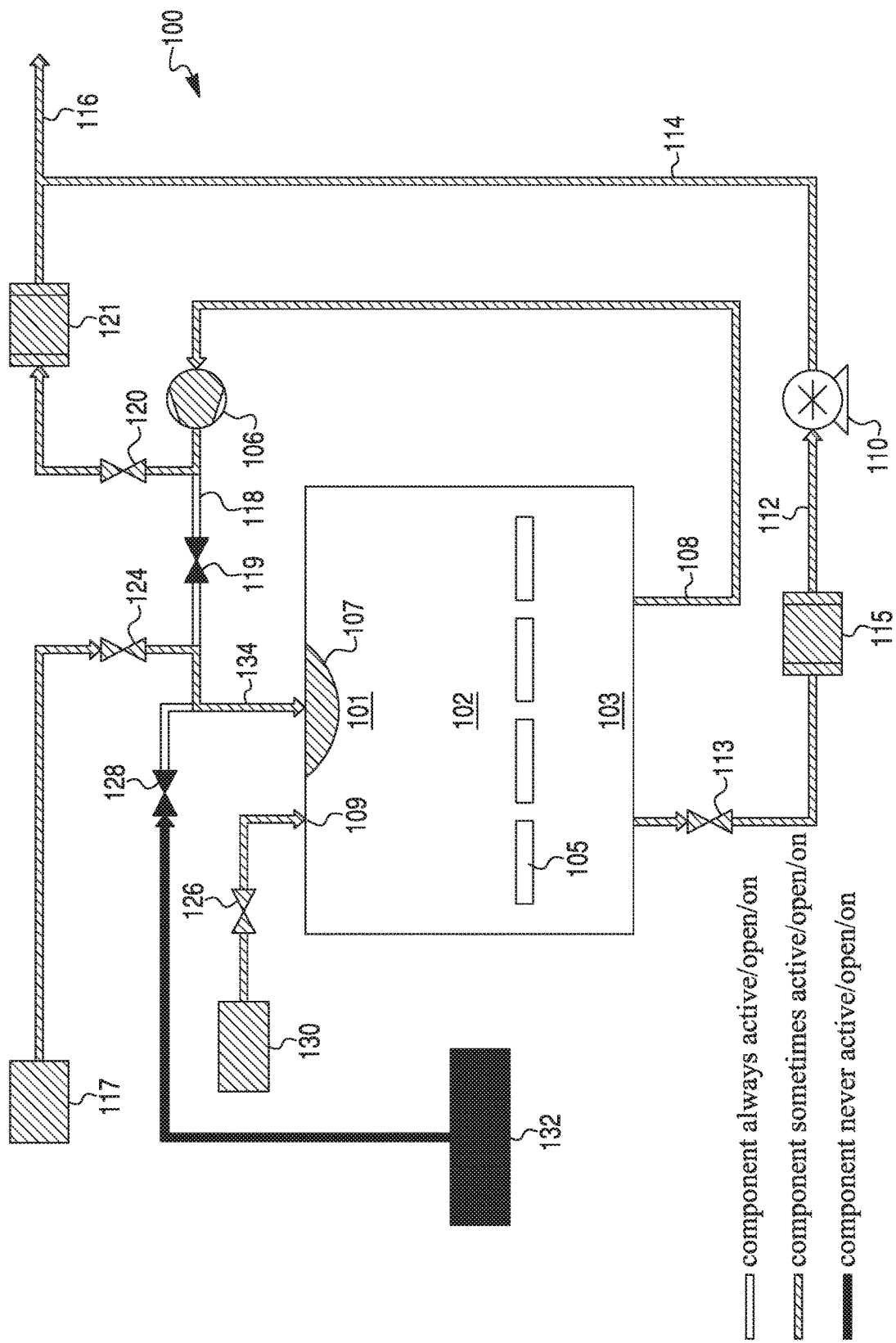

FIGS. 4A-4C depict, in schematic form, sterilization system 100, and in particular, which parts of sterilization system 100 may be active, open, or on (as opposed to inactive, closed, or off) during phases 300, 320, and 340. For clarity, controller 140 and thermal jacket 104 are not pictured.

FIG. 4A depicts, in schematic form, the various parts of sterilization system 100 in various stages of activity or inactivity during sterilization phase 300. As is shown, during sterilization phase 300, blower exit conduit 108, blower circulation conduit 118, blower 106, and recirculation valve 119 remain open, on, or active throughout sterilization phase 300. Air supply 117, air supply valve 124, exhaust valve 120, and catalytic converter 121 remain closed, off, or inactive throughout sterilization phase 300. The remaining components are sometimes open, on, or active during sterilization phase 300. The following table indicates when these components are open, on or active:

TABLE 1

| | Components | Vacuum valve 113; vacuum conduit 112; catalytic converter 115; vacuum pump 110; vacuum exhaust conduit 114; exhaust 116 | VHP injector 132; VHP injector valve 128 | Dry air supply 130; dry air supply valve 126; inlet 109 |
|---|---|---|---|---|
| Steps | Achieving vacuum level (step 302) | On/open/active | | |
| | Injecting vaporized chemical (step 304) | | On/open/active | |
| | Maintaining post-injection hold (step 306) | | | |
| | Transitioning to shallower vacuum (step 308) | | | On/open/active |
| | Maintaining post-transition hold (step 310) | | | |

FIG. 4B depicts, in schematic form, the various parts of sterilization system 100 during first aeration phase 320. As is shown, during first aeration phase 320, VHP injector 132, VHP injector valve 128, and recirculation valve 119 remain off or closed. The remaining components are sometimes open, on, or active during first aeration phase 320, as indicated in the following table:

TABLE 2

| | Components | air supply 117; air valve 124; inlet 134; distribution manifold 107; blower 106; blower exit conduit 108; exhaust valve 120; catalytic converter 121 | Vacuum conduit 112; vacuum valve 113; catalytic converter 115; vacuum pump 110; vacuum exhaust conduit 114 | Dry air supply 130; dry air supply valve 126; inlet 109 | Exhaust 116 |
|---|---|---|---|---|---|
| Steps | Achieving vacuum level (step 322) Holding the vacuum level (step 324) | | On/open/active | On/open/active | On/open/active |

TABLE 2-continued

| | | | | |
|---|---|---|---|---|
| Components | air supply 117; air valve 124; inlet 134; distribution manifold 107; blower 106; blower exit conduit 108; exhaust valve 120; catalytic converter 121 | Vacuum conduit 112; vacuum valve 113; catalytic converter 115; vacuum pump 110; vacuum exhaust conduit 114 | Dry air supply 130; dry air supply valve 126; inlet 109 | Exhaust 116 |
| Breaking the vacuum level (step 326) | | | On/open/ active | |
| Aerating and exhausting the system (step 328) | On/open/active | | | On/open/ active |

FIG. 4C depicts, in schematic form, the various parts of sterilization system 100 during second aeration phase 340. As is shown, during second aeration phase 340, air supply 117, air supply valve 124, VHP injector, VHP injector valve 128, exhaust valve 120, and catalytic converter 121 remain closed. Blower exit conduit 108, blower 108, blower circulation conduit 118, recirculation valve 119, inlet 134, and distribution manifold 107 remain open during aeration phase 340. The remaining components are sometimes open, on, or active during aeration phase 340. The following table indicates when these components are open, on or active:

TABLE 3

| | Components | Vacuum conduit 112; vacuum valve 113; catalytic converter 115; vacuum pump 110; vacuum exhaust conduit 114; exhaust 116 | Dry air supply 130; dry air supply valve 126; inlet 109 |
|---|---|---|---|
| Steps | Achieving vacuum level (step 342) | On/open/active | On/open/active |
| | Holding the vacuum level (step 344) | | |
| | Breaking the vacuum level (step 346) | | On/open/active |

In some embodiments, any or all of the above-described steps and phases may be executed automatically by sterilization system 100 as directed by, e.g., controller 140, which may be programmed or otherwise configured in advance by e.g., a user. The methods of sterilization disclosed herein may be qualified as "limited overkill" sterilization methods, in that they may ensure sterilization of a load of, e.g., PFS while minimizing impact of the sterilization method on the product.

The above description is illustrative, and is not intended to be restrictive. One of ordinary skill in the art may make numerous modification and/or changes without departing from the general scope of the invention. For example, and as has been described, the above-described embodiments (and/or aspects thereof) may be used in combination with each other. Additionally, portions of the above-described embodiments may be removed without departing from the scope of the invention. In addition, modifications may be made to adapt a particular situation or material to the teachings of the various embodiments without departing from their scope. Many other embodiments will also be apparent to those of skill in the art upon reviewing the above description.

What is claimed is:

1. A sterilization method comprising:
   creating a turbulent flow within a chamber; and
   while maintaining the turbulent flow, performing a sterilization pulse comprising:
      maintaining a sterilization pressure within the chamber for at least 5 minutes;
      introducing vaporized hydrogen peroxide (VHP) into the chamber;
      allowing the VHP to circulate within the chamber for at least 5 minutes, wherein allowing the VHP to circulate within the chamber includes removing the VHP from a lower interior of the chamber and re-introducing the VHP into an upper interior of the chamber; and
      introducing dry gas into the chamber, wherein the dry gas has a dew point of −10° C. or lower
   wherein, during the sterilization pulse, a condensation layer forms on a primary packaging component.

2. The method of claim 1, wherein the sterilization pressure is between about 400 millibars and about 800 millibars.

3. The method of claim 1, further comprising performing between 2 and 5 sterilization pulses.

4. The method of claim 1, wherein the dry gas includes nitrogen.

5. The method of claim 1, wherein the turbulent flow is maintained using a blower external to the chamber.

6. The method of claim 1, further comprising performing at least 2 sterilization pulses, and wherein each sterilization pulse further comprises creating the sterilization pressure within the chamber prior to introducing VHP into the chamber.

7. The method of claim 1, further comprising positioning a primary packaging component within the chamber, wherein the primary packaging component is configured for receiving a formulated drug substance including an antibody.

8. The method of claim 1, wherein the dry gas is a first dry gas having a dew point of −10° C. or lower, and further comprising performing an aeration pulse comprising:
achieving a first aeration pressure of between about 400 millibars and about 800 millibars in the chamber;
increasing the pressure within the chamber to a second aeration pressure higher than the first aeration pressure; and
simultaneously exhausting the gas from the chamber while introducing room air, air having a dew point of −10° C. or lower, or a second dry gas having a dew point of −10° C. or lower, into the chamber.

9. The method of claim 8, further comprising halting the turbulent flow in the chamber prior to performing the aeration pulse.

10. The method of claim 8, further comprising performing between 2 and 35 aeration pulses.

11. The method of claim 8, wherein the steps of (a) introducing room air, air having a dew point of −10° C. or lower, or a second dry gas having a dew point of −10° C. or lower, into the chamber and (b) achieving the first aeration pressure, are performed simultaneously.

12. The method of claim 8, wherein the second aeration pressure is between about 550 millibars and about 1100 millibars.

13. The method of claim 1, further comprising maintaining a temperature of between about 25° C. and about 60° C. within the chamber while performing the sterilization pulse.

14. The method of claim 1, wherein introducing VHP into the chamber comprises introducing between about 50 g and about 700 g of VHP into the chamber.

15. A sterilization method comprising:
creating a turbulent flow within a chamber;
while maintaining the turbulent flow, performing a sterilization pulse comprising:
maintaining a sterilization pressure within the chamber of between about 400 millibars and about 800 millibars for at least 5 minutes;
introducing vaporized hydrogen peroxide (VHP) into the chamber;
allowing the VHP to circulate within the chamber for at least 5 minutes, wherein allowing the VHP to circulate within the chamber includes removing the VHP from a lower interior of the chamber and re-introducing the VHP into an upper interior of the chamber; and
introducing a first gas into the chamber;
halting the turbulent flow within the chamber; and
performing an aeration pulse comprising:
introducing a second gas into the chamber;
maintaining a first aeration pressure in the chamber for at least 5 minutes;
increasing the pressure within the chamber to a second aeration pressure higher than the first aeration pressure; and
exhausting the second gas from the chamber
wherein, during the sterilization pulse, condensation comprising hydrogen peroxide forms in the chamber.

16. The method of claim 15, wherein the first aeration pressure is between about 400 millibars and about 800 millibars, and wherein the second aeration pressure is between about 550 millibars and about 1100 millibars.

17. The method of claim 15, wherein the first gas includes one of nitrogen or a gas having a dew point of −10° C. or lower, and wherein the second gas includes one of nitrogen, a gas having a dew point of −10° C. or lower, or air.

18. The method of claim 15, further comprising performing a drying pulse after performing the aeration pulse, wherein the drying pulse comprises:
introducing a third gas into the chamber;
maintaining a first drying pressure in the chamber for at least 1 minute; and
maintaining a second drying pressure in the chamber for at least 1 minute.

19. The method of claim 18, wherein the second gas is air, and the third gas is one of nitrogen or a gas having a dew point of −10° C. or lower.

20. The method of claim 18, wherein at least 99% of the VHP introduced into the chamber during the sterilization pulse is removed from the chamber by the conclusion of the drying pulse.

21. The method of claim 15, wherein introducing VHP into the chamber includes introducing between about 50 g and about 700 g of VHP into the chamber.

22. A sterilization method comprising:
creating a turbulent flow within a chamber;
while maintaining the turbulent flow, performing a plurality of sterilization pulses, wherein each sterilization pulse includes:
maintaining a sterilization pressure within the chamber of between about 400 millibars and about 800 millibars for at least 5 minutes;
introducing vaporized hydrogen peroxide (VHP) into the chamber;
allowing the VHP to circulate within the chamber for at least 5 minutes, wherein allowing the VHP to circulate within the chamber includes removing the VHP from a lower interior of the chamber and re-introducing the VHP into an upper interior of the chamber; and
introducing one of nitrogen or a gas having a dew point of −10° C. or lower into the chamber;
performing a plurality of aeration pulses after performing the plurality of sterilization pulses, wherein each aeration pulse includes:
introducing one of air, nitrogen, or a gas having a dew point of −10° C. or lower into the chamber;
maintaining a first aeration pressure of between about 400 and about 800 millibars in the chamber for at least 5 minutes;
increasing the pressure within the chamber to a second aeration pressure of between about 550 and 1100 millibars; and
exhausting the second gas from the chamber; and
performing a plurality of drying pulses after performing the plurality of aeration pulses, wherein each of the plurality of drying pulses includes:
introducing one of nitrogen or a gas having a dew point of −10° C. or lower into the chamber;
maintaining a first drying pressure of between about 500 and about 850 millibars in the chamber for at least 1 minute; and
maintaining a second drying pressure higher than the first drying pressure in the chamber for at least 1 minute
wherein, during one of the sterilization pulses, VHP condenses on a primary packaging component within the chamber.

23. The method of claim 22, wherein the plurality of sterilization pulses includes between 2 and 5 pulses.

24. The method of claim 22, wherein each drying pulse includes introducing a gas having a dew point of 10° C. or lower into the chamber.

25. The method of claim 22, wherein creating the turbulent flow in the chamber comprises activating a blower external to the chamber.

\* \* \* \* \*